(12) United States Patent
Berg et al.

(10) Patent No.: US 8,532,775 B2
(45) Date of Patent: Sep. 10, 2013

(54) MODULAR MEDICAL DEVICE PROGRAMMER

(75) Inventors: Richard O. Berg, Maple Grove, MN (US); Danilo Marchesin, Dairago (IT); Gerald M. Herman, Fridley, MN (US); Leon W. Durivage, III, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 130 days.

(21) Appl. No.: 13/098,052

(22) Filed: Apr. 29, 2011

(65) Prior Publication Data

US 2012/0215277 A1 Aug. 23, 2012

Related U.S. Application Data

(60) Provisional application No. 61/444,557, filed on Feb. 18, 2011.

(51) Int. Cl.
*A61N 1/08* (2006.01)
(52) U.S. Cl.
USPC .................................. 607/32; 607/30; 607/31
(58) Field of Classification Search
USPC ...................................................... 607/30–32
See application file for complete search history.

(56) References Cited

U.S. PATENT DOCUMENTS

| | | |
|---|---|---|
| 3,631,847 A | 1/1972 | Hobbs, II |
| 3,942,535 A | 3/1976 | Schulman |
| 4,208,008 A | 6/1980 | Smith |
| 4,270,532 A | 6/1981 | Franetzki et al. |
| 4,282,872 A | 8/1981 | Franetzki et al. |
| 4,304,238 A | 12/1981 | Fischer |
| 4,365,633 A | 12/1982 | Loughman et al. |
| 4,373,527 A | 2/1983 | Fischell |
| 4,395,259 A | 7/1983 | Prestele et al. |
| 4,443,218 A | 4/1984 | DeCant, Jr. et al. |
| 4,494,950 A | 1/1985 | Fischell |
| 4,542,532 A | 9/1985 | McQuilkin |

(Continued)

FOREIGN PATENT DOCUMENTS

| | | |
|---|---|---|
| DE | 43 29 229 | 3/1995 |
| EP | 0750921 A2 | 1/1997 |

(Continued)

OTHER PUBLICATIONS

Invitation to Pay Additional Fees from international application No. PCT/US2011/034657, dated Oct. 10, 2011, 4 pp.
Khalessi et al., "Automated, patient interactive spinal cord stimulator adjustment: A cost-minimization analysis," Neurosurgery, 53:501-502, Aug. 2003.
North et al., "Automated, patient-interactive spinal cord stimulator adjustment: A randomized, controlled trial," Neurosurgery 52:572-580, Mar. 2003.
Fowler, "Neurological Stimulation System," Proceedings AAMI 21st Annual Meeting, Apr. 12-16, 1986, p. 27.

(Continued)

*Primary Examiner* — Joseph Stoklosa

(57) ABSTRACT

A medical device programmer comprises a medical device module and a computer module. The medical device module comprises a telemetry module that wirelessly communicates with an implantable medical device (IMD) and a medical device module processor communicates with the IMD via the telemetry module. The computer module housing mates with the medical device module housing to form a congruent external surface of the programmer. The computer module comprises a user interface including a touchscreen that displays data received from the IMD and receives input from a user, a memory that stores selectable patient therapy parameters for the IMD, a computer module interface in electrical communication with the medical device module interface, and a computer module processor that communicates with the medical device module. The medical device module processor forwards communications between the computer module processor and the IMD via the medical device module interface and the telemetry module.

21 Claims, 13 Drawing Sheets

(56) References Cited

U.S. PATENT DOCUMENTS

| | | |
|---|---|---|
| 4,550,731 A | 11/1985 | Batina et al. |
| 4,550,732 A | 11/1985 | Batty, Jr. et al. |
| 4,559,037 A | 12/1985 | Franetzki et al. |
| 4,562,751 A | 1/1986 | Nason et al. |
| 4,564,012 A | 1/1986 | Shimada et al. |
| 4,573,994 A | 3/1986 | Fischell et al. |
| 4,587,970 A | 5/1986 | Holley et al. |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, II |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 4,926,865 A | 5/1990 | Oman |
| 5,019,974 A | 5/1991 | Beckers |
| 5,050,612 A | 9/1991 | Matsumura |
| 5,078,683 A | 1/1992 | Sancoff et al. |
| 5,100,380 A | 3/1992 | Epstein et al. |
| 5,158,078 A | 10/1992 | Bennett et al. |
| 5,226,413 A | 7/1993 | Bennett et al. |
| 5,246,867 A | 9/1993 | Lakowicz et al. |
| 5,299,571 A | 4/1994 | Mastrototaro |
| 5,307,263 A | 4/1994 | Brown |
| 5,317,506 A | 5/1994 | Coutre et al. |
| 5,338,157 A | 8/1994 | Blomquist |
| 5,339,821 A | 8/1994 | Fujimoto |
| 5,341,291 A | 8/1994 | Roizen et al. |
| 5,342,789 A | 8/1994 | Chick et al. |
| 5,350,407 A | 9/1994 | McClure et al. |
| 5,350,411 A | 9/1994 | Ryan et al. |
| 5,357,427 A | 10/1994 | Langen et al. |
| 5,368,562 A | 11/1994 | Blomquist et al. |
| 5,376,070 A | 12/1994 | Purvis et al. |
| 5,383,915 A | 1/1995 | Adams |
| 5,390,671 A | 2/1995 | Lord et al. |
| 5,391,250 A | 2/1995 | Cheney, II et al. |
| 5,417,222 A | 5/1995 | Dempsey et al. |
| 5,456,692 A | 10/1995 | Smith, Jr. et al. |
| 5,482,473 A | 1/1996 | Lord et al. |
| 5,485,408 A | 1/1996 | Blomquist |
| 5,503,770 A | 4/1996 | James et al. |
| 5,507,288 A | 4/1996 | Böcker et al. |
| 5,512,246 A | 4/1996 | Russell et al. |
| 5,568,806 A | 10/1996 | Cheney, II et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,594,638 A | 1/1997 | Iliff |
| 5,607,458 A | 3/1997 | Causey, III et al. |
| 5,609,060 A | 3/1997 | Dent |
| 5,615,318 A | 3/1997 | Matsuura |
| 5,626,144 A | 5/1997 | Tacklind et al. |
| 5,628,310 A | 5/1997 | Rao et al. |
| 5,643,212 A | 7/1997 | Coutre et al. |
| 5,653,735 A | 8/1997 | Chen et al. |
| 5,660,176 A | 8/1997 | Iliff |
| 5,665,065 A | 9/1997 | Colman et al. |
| 5,678,571 A | 10/1997 | Brown |
| 5,683,432 A | 11/1997 | Goedeke et al. |
| 5,685,844 A | 11/1997 | Marttila |
| 5,687,734 A | 11/1997 | Dempsey et al. |
| 5,690,690 A | 11/1997 | Nappholz et al. |
| 5,701,894 A | 12/1997 | Cherry et al. |
| 5,704,366 A | 1/1998 | Tacklind et al. |
| 5,713,856 A | 2/1998 | Eggers et al. |
| 5,716,384 A * | 2/1998 | Snell .......................... 607/30 |
| 5,752,977 A | 5/1998 | Grevious et al. |
| 5,764,159 A | 6/1998 | Neftel |
| 5,772,635 A | 6/1998 | Dastur et al. |
| 5,779,655 A | 7/1998 | Holden |
| 5,788,669 A | 8/1998 | Peterson |
| 5,792,201 A | 8/1998 | Causey, III et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,898,679 A | 4/1999 | Brederveld et al. |
| 5,899,855 A | 5/1999 | Brown |
| 5,913,310 A | 6/1999 | Brown |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,938,690 A | 8/1999 | Law et al. |
| 5,940,801 A | 8/1999 | Brown |
| 5,954,643 A | 9/1999 | Van Antwerp et al. |
| 5,956,501 A | 9/1999 | Brown |
| 5,960,403 A | 9/1999 | Brown |
| 5,961,451 A | 10/1999 | Reber et al. |
| 5,997,476 A | 12/1999 | Brown |
| 6,009,339 A | 12/1999 | Bentsen et al. |
| 6,011,984 A | 1/2000 | VanAntwerp et al. |
| 6,032,119 A | 2/2000 | Brown et al. |
| 6,101,478 A | 8/2000 | Brown |
| 6,103,033 A | 8/2000 | Say et al. |
| 6,134,461 A | 10/2000 | Say et al. |
| 6,168,563 B1 | 1/2001 | Brown |
| 6,175,752 B1 | 1/2001 | Say et al. |
| 6,177,905 B1 | 1/2001 | Welch |
| 6,246,992 B1 | 6/2001 | Brown |
| 6,248,067 B1 | 6/2001 | Causey, III et al. |
| 6,249,703 B1 | 6/2001 | Stanton et al. |
| 6,295,506 B1 | 9/2001 | Heinonen et al. |
| 6,308,102 B1 | 10/2001 | Sieracki et al. |
| 6,478,736 B1 | 11/2002 | Mault |
| 6,480,745 B2 | 11/2002 | Nelson et al. |
| 6,516,227 B1 | 2/2003 | Meadows et al. |
| 6,532,628 B2 | 3/2003 | Kim |
| 6,554,798 B1 | 4/2003 | Mann et al. |
| 6,558,320 B1 | 5/2003 | Causey, III et al. |
| 6,577,899 B2 | 6/2003 | Lebel et al. |
| 6,580,948 B2 * | 6/2003 | Haupert et al. .................. 607/60 |
| 6,597,951 B2 | 7/2003 | Kramer et al. |
| 6,609,032 B1 | 8/2003 | Woods et al. |
| 6,622,045 B2 | 9/2003 | Snell et al. |
| 6,641,533 B2 | 11/2003 | Causey, III et al. |
| 6,654,027 B1 | 11/2003 | Hernandez |
| 6,659,968 B1 | 12/2003 | McClure |
| 6,665,565 B1 | 12/2003 | Stomberg et al. |
| 6,804,558 B2 | 10/2004 | Haller et al. |
| 6,868,309 B1 | 3/2005 | Begelman |
| 6,878,112 B2 | 4/2005 | Linberg et al. |
| 6,895,280 B2 | 5/2005 | Meadows et al. |
| 6,978,181 B1 | 12/2005 | Snell |
| 7,015,935 B2 | 3/2006 | Herget et al. |
| 7,043,305 B2 | 5/2006 | KenKnight et al. |
| 7,060,031 B2 | 6/2006 | Webb et al. |
| 7,065,409 B2 | 6/2006 | Mazar |
| 7,142,923 B2 | 11/2006 | North et al. |
| 7,146,219 B2 | 12/2006 | Sieracki et al. |
| 7,155,290 B2 | 12/2006 | Von Arx et al. |
| 7,181,286 B2 | 2/2007 | Sieracki et al. |
| 7,216,000 B2 | 5/2007 | Sieracki et al. |
| 7,286,894 B1 | 10/2007 | Grant et al. |
| 7,373,206 B2 | 5/2008 | Sieracki et al. |
| 7,489,970 B2 | 2/2009 | Lee et al. |
| 7,499,048 B2 | 3/2009 | Sieracki et al. |
| 7,610,099 B2 | 10/2009 | Almendinger et al. |
| 7,657,319 B2 | 2/2010 | Goetz et al. |
| 7,742,821 B1 | 6/2010 | Vamos et al. |

| | | | |
|---|---|---|---|
| 7,848,819 B2 | 12/2010 | Goetz et al. | |
| 7,885,712 B2 | 2/2011 | Goetz et al. | |
| 7,899,546 B2 | 3/2011 | Sieracki et al. | |
| 2001/0041920 A1 | 11/2001 | Starkweather et al. | |
| 2002/0016568 A1 | 2/2002 | Lebel et al. | |
| 2002/0049480 A1 | 4/2002 | Lebel et al. | |
| 2002/0123673 A1 | 9/2002 | Webb et al. | |
| 2002/0133207 A1 | 9/2002 | Thomas et al. | |
| 2003/0041192 A1 | 2/2003 | Teng et al. | |
| 2003/0088290 A1 | 5/2003 | Spinelli et al. | |
| 2003/0109905 A1 | 6/2003 | Mok et al. | |
| 2003/0130708 A1 | 7/2003 | Von Arx et al. | |
| 2003/0171789 A1 | 9/2003 | Malek et al. | |
| 2003/0177031 A1 | 9/2003 | Malek | |
| 2004/0055114 A1 | 3/2004 | Lu | |
| 2004/0073095 A1 | 4/2004 | Causey, III et al. | |
| 2004/0138518 A1 | 7/2004 | Rise et al. | |
| 2004/0138724 A1 | 7/2004 | Sieracki et al. | |
| 2004/0143302 A1 | 7/2004 | Sieracki et al. | |
| 2004/0167587 A1 | 8/2004 | Thompson | |
| 2004/0199215 A1 | 10/2004 | Lee et al. | |
| 2004/0215286 A1 | 10/2004 | Stypulkowski | |
| 2004/0225337 A1* | 11/2004 | Housworth et al. | 607/60 |
| 2004/0260363 A1 | 12/2004 | Arx et al. | |
| 2005/0010269 A1 | 1/2005 | Lebel et al. | |
| 2005/0021108 A1 | 1/2005 | Klosterman et al. | |
| 2005/0277999 A1 | 12/2005 | Strother et al. | |
| 2005/0283198 A1 | 12/2005 | Haubrich et al. | |
| 2006/0113382 A1 | 6/2006 | Singgih et al. | |
| 2006/0161213 A1 | 7/2006 | Patel | |
| 2006/0190047 A1 | 8/2006 | Gerber et al. | |
| 2007/0156033 A1* | 7/2007 | Causey et al. | 600/300 |
| 2008/0055826 A1 | 3/2008 | Smith et al. | |
| 2008/0140161 A1 | 6/2008 | Goetz et al. | |
| 2008/0140162 A1 | 6/2008 | Goetz et al. | |
| 2008/0140163 A1 | 6/2008 | Keacher et al. | |
| 2009/0157137 A1 | 6/2009 | Gilkerson et al. | |
| 2010/0094132 A1* | 4/2010 | Hansen et al. | 600/443 |
| 2010/0228323 A1 | 9/2010 | Vamos et al. | |
| 2010/0280578 A1 | 11/2010 | Skelton et al. | |
| 2012/0036679 A1 | 2/2012 | Chen | |
| 2012/0176741 A1* | 7/2012 | Wu et al. | 361/679.09 |

FOREIGN PATENT DOCUMENTS

| | | |
|---|---|---|
| EP | 0753327 A2 | 1/1997 |
| EP | 0 806 738 A1 | 11/1997 |
| EP | 0 880 936 A2 | 12/1998 |
| WO | WO 94/01039 A1 | 1/1994 |
| WO | WO 97/21456 A1 | 6/1997 |
| WO | WO 97/28736 A1 | 8/1997 |
| WO | WO 98/20439 A1 | 5/1998 |
| WO | WO 98/24358 A2 | 6/1998 |
| WO | WO 98/42407 A1 | 10/1998 |
| WO | WO 98/49659 A2 | 11/1998 |
| WO | WO 98/59487 A1 | 12/1998 |
| WO | WO 99/08183 A1 | 2/1999 |
| WO | WO 99/10801 A1 | 3/1999 |
| WO | WO 99/18532 A1 | 4/1999 |
| WO | WO 99/22236 A1 | 5/1999 |
| WO | WO 99/56613 A1 | 11/1999 |
| WO | WO 00/19887 A1 | 4/2000 |
| WO | WO 00/78210 A1 | 12/2000 |
| WO | WO 01/28416 A1 | 4/2001 |
| WO | WO 01/28495 A2 | 4/2001 |
| WO | WO 01/39089 A1 | 5/2001 |
| WO | 0145793 A1 | 6/2001 |
| WO | WO 01/52718 A2 | 7/2001 |
| WO | WO 01/56454 A2 | 8/2001 |
| WO | 0187413 A1 | 11/2001 |
| WO | WO 02/057994 A2 | 7/2002 |
| WO | WO 03/092769 A2 | 11/2003 |
| WO | 2008051983 A2 | 5/2008 |
| WO | 2009062938 A1 | 5/2009 |
| WO | 2010143045 A2 | 12/2010 |

OTHER PUBLICATIONS

Fowler et al., "Patient-interactive PC interface to implanted, multichannel stimulators," Proceedings of 39th Annual Conference on Engineering in Medicine and Biology, p. 380, 1986.

North et al., "Computer-controlled, patient-interactive, multichannel, implanted neurological stimulators," Applied Neurophysiology, 50:39-41, 1987.

North et al., "Computer-controlled, multichannel, implanted neurological stimulation system: Clinical assessment," Pain (Suppl.), 5:S83, 1990.

Fowler et al., "Computer-optimized neurological stimulation," Proc. Ann. Internat. Conf. IEEE Engineering Medicine and Biology Soc., 13:1692-1693, 1991.

Fowler et al., "Computer-optimized neurostimulation," APL Technical Digest, 12:192-197, 1991.

North et al., "Spinal cord stimulation for chronic intractable pain: superiority of 'multi-channel' devices," Pain, V44, pp. 119-130, 1991.

North et al., "Computer-controlled, patient-interactive neurological stimulation system" (Abstract) Acta Neurochir., 117:90, 1992.

North et al., "Patient interactive, computer-controlled neurological stimulation system: clinical efficacy in spinal cord stimulator adjustment," Journal of Neurosurgery, 76:967-972, 1992.

North et al., "Automated 'pain drawing' analysis by computer-controlled, patient-interactive neurological stimulation system," Pain, 50:51-57, 1992.

North, "Spinal Cord Stimulation for Chronic Intractable Pain," Electrical and Magnetic Stimulation of the Brain and Spinal Cord, pp. 289-301, 1993.

North, "The Role of Spinal Cord Stimulation in Contemporary Pain Management," APS Journal, vol. 2, No. 2, pp. 91-99, 1993.

North et al., "Spinal cord stimulation for chronic, intractable pain: Experience over two decades," Neurosurgery, 32:384-395, 1993.

North et al., "Patient-interactive, microprocessor-controlled neurological stimulation system" (abstract), Stereotactic and Functional Neurosurgery, 62:309-315, 1994.

North et al., "Consensus conference on the neurosurgical management of pain," Neurosurgery, 34:756-761, 1994.

North et al., "A prospective, randomized study of spinal cord stimulation versus reoperation for the failed back surgery syndrome," Stereotactic and Functional Neurosurgery, 62:267-272, 1994.

North et al., "Spinal Cord Stimulation for Chronic Pain," Functional Neurosurgery, vol. 6, No. 1, pp. 145-155, Jan. 1995.

North et al., "Spinal cord stimulation for chronic intractable pain," Spinal Cord Stimulation II, pp. 49-63, Darmstadt, Steinkopff, 1995.

North et al., "Artificial neural networks: Application to electrical stimulation of the human nervous system," (abstract) Stereotactic and Functional Neurosurgery, 65:161, 1995.

North et al., "Prognostic value of psychological testing in spinal cord stimulation patients: A prospective study," Neurosurgery, 39:301-311, 1996.

North et al., "Specificity of diagnostic nerve blocks: A prospective, randomized study of sciatica due to lumbosacral spine disease," Pain 65:77-85, 1996.

North et al., "Artificial neural networks: Application to electrical stimulation of the human nervous system," Neurosurgical Focus, 2(1:1): 1-5, 1997.

Alo et al., "Computer Assisted and Patient Interactive Programming of Dual Octrode Spinal Cord Stimulation in the Treatment of Chronic Pain," Neuromodulation, vol. 1, No. 1, pp. 30-45, 1998.

North et al., "Patient-interactive, microprocessor-controlled neurological stimulation system," Neuromodulation, 1(4): 185-193, 1998.

U.S. Appl. No. 13/015,230, by Jeffrey M. Sieracki, filed Jan. 27, 2011.

U.S. Appl. No. 09/334,996, by James D. Causey, III, filed Jun. 17, 1999.

U.S. Appl. No. 09/377,472, by Alfred E. Mann, filed Aug. 19, 1999.

U.S. Appl. No. 13/098,099, by Richard O. Berg, filed Apr. 29, 2011.

International Search Report and Written Opinion of international application No. PCT/US2011/034657, dated Dec. 12, 2011, 15 pp.

Notice of Allowance from U.S. Appl. No. 13/098,099, dated Nov. 26, 2012, 11 pp.

* cited by examiner

MODULAR MEDICAL DEVICE PROGRAMMER

This application claims the benefit of U.S. Provisional Application No. 61/444,557, entitled, "MODULAR MEDICAL DEVICE PROGRAMMER," and filed on Feb. 18, 2011, the entire content of which is incorporated herein by reference.

TECHNICAL FIELD

The disclosure relates to medical devices and, more particularly, to programming for implantable medical devices (IMDs).

BACKGROUND

Some types of IMDs provide therapeutic electrical stimulation to tissue of a patient via electrodes of one or more implantable leads. Examples of such IMDs include implantable cardiac pacemakers, cardioverter-defibrillators, and implantable pulse generators used to deliver neurostimulation therapies. In some examples, an IMD may deliver electrical stimulation to the tissue via electrodes of implantable leads in the form of pacing stimulation, cardioversion stimulation, defibrillation stimulation, or cardiac resynchronization stimulation. In some cases, electrodes carried by the implantable leads may be used to sense one or more physiological signals to monitor the condition of a patient and/or to control delivery of therapeutic electrical stimulation based on the sensed signals.

Typically, a clinician uses a programming device, e.g., a clinician programmer, to program aspects of the operation of an IMD after it has been implanted within a patient. Programming devices are computing devices capable of communicating with IMDs through patient body tissue via device telemetry. To facilitate communication with an IMD, a programming device may be coupled to a telemetry head that is placed on the surface of the patient at a position proximate to location of the IMD within the patient.

IMDs may provide a variety of therapy delivery and/or patient monitoring modes, which may be selected and configured by the clinician during a programming session or by a patient during therapy sessions, i.e., the time periods in-between programming sessions. During a programming session, the clinician may select values for a variety of programmable parameters, threshold values, or the like, that control aspects the delivery of therapy. The clinician may also specify patient-selectable therapy and or sensing parameters for therapy sessions.

SUMMARY

This disclosure includes techniques providing a programmer including a computer module and a mating medical device module. The computer module includes a user interface with a touchscreen, and the patient programming module includes telemetry and/or electrodcardiography (ECG) functions of the programmer. The computer module may be configured to store therapy delivery and sensing parameters and history as well as other patient data. The computer module and the medical device module may mate to form a congruent external surface of the programmer.

In one example, a medical device programmer comprises a medical device module and a computer module. The medical device module comprises a medical device module housing including mating features, a telemetry module that wirelessly communicates with an implantable medical device (IMD) that delivers therapy to a patient, a medical device module interface, and a medical device module processor communicates with the IMD via the telemetry module. The computer module comprises a computer module housing including complimentary mating features that compliment the mating features of the medical device module housing such that the computer module housing and the medical device module housing combine to form a congruent external surface of the programmer. The computer module further comprises a user interface including a touchscreen that displays data received from the IMD and receives input from a user, a memory that stores selectable patient therapy parameters for the IMD, a computer module interface in electrical communication with the medical device module interface, and a computer module processor that communicates with the medical device module via the computer module interface. The medical device module processor forwards communications between the computer module processor and the IMD via the medical device module interface and the telemetry module. In a further example, the programmer is included in a system further comprising the IMD.

In another example, a medical device programmer comprises a medical device module and a computer module. The medical device module comprises a medical device module housing including mating features, a telemetry module that wirelessly communicates with an implantable medical device (IMD) that delivers therapy to a patient, an telemetry head cable bay with a telemetry head cable bay door in the medical device module housing, the telemetry head cable door providing access to the telemetry head cable bay, a telemetry head cable interface connector adapted to be coupled with a telemetry head cable, wherein the telemetry head cable interface connector is within the telemetry head cable bay, an electrocardiogram (ECG) module including an ECG cable interface connector adapted to be coupled with an ECG cable and including ECG signal interface circuitry that converts analog ECG signals from the ECG cable interface connector to digital ECG signals that correspond to the analog ECG signals, an ECG cable bay with an ECG cable bay door in the medical device module housing, the ECG cable bay door providing access to the ECG cable bay, wherein the ECG cable interface connector is within the ECG cable bay, a medical device module interface, and a medical device module processor communicates with the IMD via the telemetry module. The computer module comprises a computer module housing including complimentary mating features that compliment the mating features of the medical device module housing such that the computer module housing and the medical device module housing combine to form a congruent external surface of the programmer, a user interface including a touchscreen that displays data received from the IMD and receives input from a user, a memory that stores selectable patient therapy parameters for the IMD, a computer module interface in electrical communication with the medical device module interface, a computer module processor that communicates with the medical device module via the computer module interface, and a rechargeable power source. The medical device module is powered by the rechargeable power source of the computer module. The medical device module processor forwards communications between the computer module processor and the IMD via the medical device module interface and the telemetry module. In a further example, the programmer is included in a system further comprising the IMD.

The details of one or more examples are set forth in the accompanying drawings and the description below. Other features, objects, and advantages will be apparent from the description and drawings, and from the claims.

DETAILED DESCRIPTION

Figure 1:
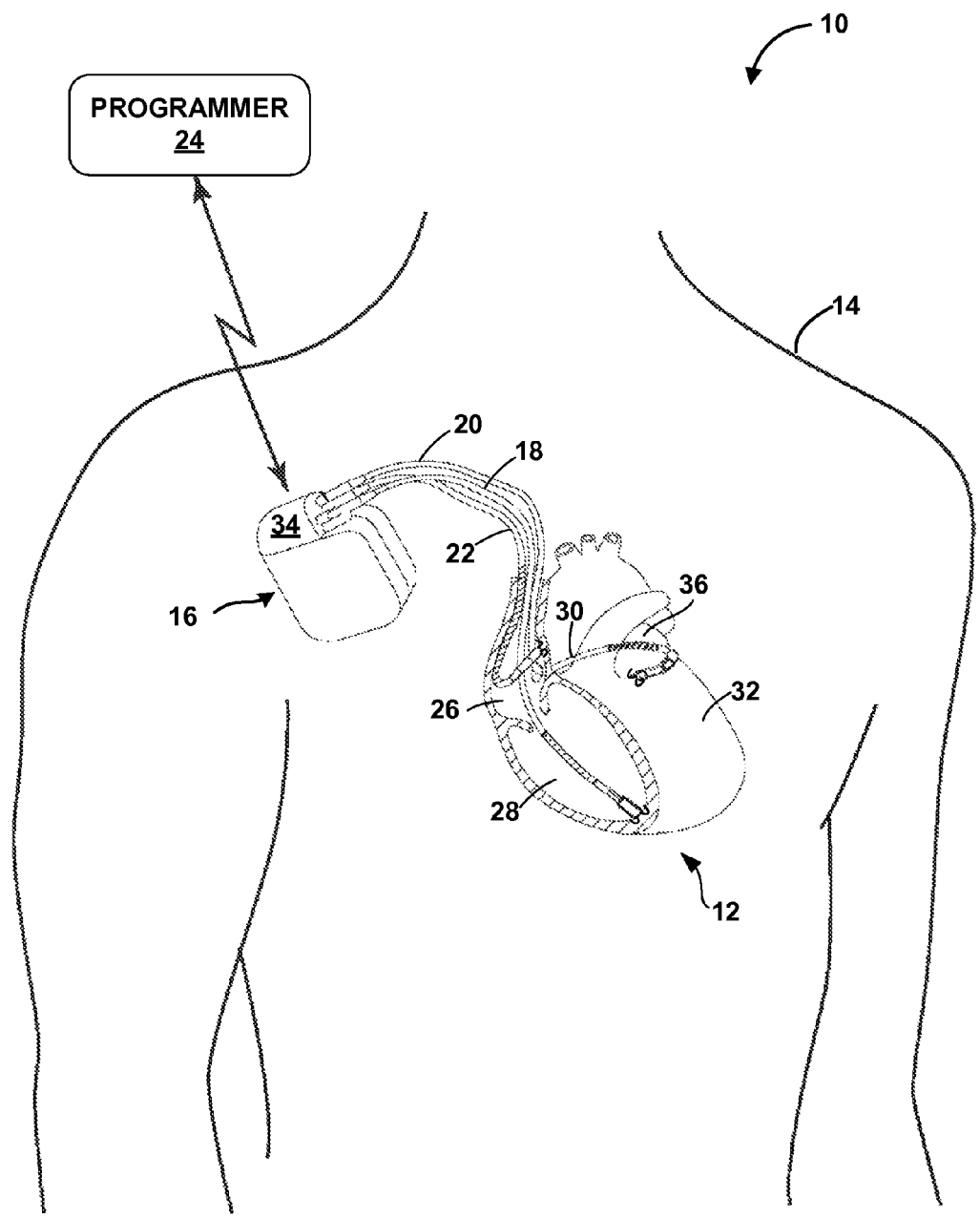
FIG. 1 is a conceptual diagram illustrating an example therapy system comprising a programmer and an IMD coupled to a plurality of leads that may be used to monitor one or more physiological parameters of a patient and/or provide therapy to the heart of a patient.

FIG. 1 is a conceptual diagram illustrating an example therapy system 10 that may be used to monitor one or more physiological parameters of patient 14 and/or to provide therapy to heart 12 of patient 14. Therapy system 10 includes IMD 16, which is coupled to medical leads 18, 20, and 22, and programmer 24, which is in wireless communication with IMD 16.

In one example, IMD 16 may be an implantable cardiac stimulator that provides electrical signals to heart 12 via electrodes coupled to one or more of leads 18, 20, and 22. IMD 16 is one example of an electrical stimulation generator, and is configured attach to the proximal end of medical leads 18, 20, and 22. In other examples, in addition to or alternatively to pacing therapy, IMD 16 may deliver neurostimulation signals. In some examples, IMD 16 may also include cardioversion and/or defibrillation functionalities. In another example, IMD 16 may include an infusion device such as an implantable drug pump that delivers a therapy fluid to a patient. In other examples, IMD 16 may not provide any therapy delivery functionalities and, instead, may be a dedicated monitoring device. Patient 14 is ordinarily, but not necessarily, a human patient.

Medical leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), right atrium 26, and into right ventricle 28. RV lead 18 may be used to deliver RV pacing to heart 12. Left ventricular (LV) lead 20 extends through one or more veins, the vena cava, right atrium 26, and into the coronary sinus 30 to a region adjacent to the free wall of left ventricle 32 of heart 12. LV lead 20 may be used to deliver LV pacing to heart 12. Right atrial (RA) lead 22 extends through one or more veins and the vena cava, and into the right atrium 26 of heart 12. RA lead 22 may be used to deliver RA pacing to heart 12.

In some examples, system 10 may additionally or alternatively include one or more leads or lead segments (not shown in FIG. 1) that deploy one or more electrodes within the vena cava or other vein, or within or near the aorta. Furthermore, in another example, system 10 may additionally or alternatively include one or more additional intravenous or extravascular leads or lead segments that deploy one or more electrodes epicardially, e.g., near an epicardial fat pad, or proximate to the vagus nerve. In other examples, system 10 need not include one of ventricular leads 18 and 20.

IMD 16 may sense electrical signals attendant to the depolarization and repolarization of heart 12 via electrodes (described in further detail with respect to FIG. 4) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar.

IMD 16 may also provide neurostimulation therapy, defibrillation therapy and/or cardioversion therapy via electrodes located on at least one of the leads 18, 20, 22. For example, IMD 16 may deliver defibrillation therapy to heart 12 in the form of electrical pulses upon detecting ventricular fibrillation of ventricles 28 and 32. In some examples, IMD 16 may be programmed to deliver a progression of therapies, e.g., pulses with increasing energy levels, until a fibrillation of heart 12 is stopped. As another example, IMD 16 may deliver cardioversion or anti-tachycardia pacing (ATP) in response to detecting ventricular tachycardia, such as tachycardia of ventricles 28 and 32.

Leads 18, 20, 22 may be electrically coupled to a signal generator and a sensing module of IMD 16 via connector block 34. In some examples, proximal ends of leads 18, 20, 22 may include electrical contacts that electrically couple to respective electrical contacts within connector block 34 of IMD 16. In some examples, a single connector, e.g., an IS-4 or DF-4 connector, may connect multiple electrical contacts to connector block 34. In addition, in some examples, leads 18, 20, 22 may be mechanically coupled to connector block 34 with the aid of set screws, connection pins, snap connectors, or another suitable mechanical coupling mechanism.

A user, such as a physician, technician, surgeon, electrophysiologist, other clinician, or patient, interacts with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD 16. For example, the user may use programmer 24 to retrieve information from IMD 16 regarding the rhythm of heart 12, trends therein over time, or arrhythmic episodes.

As an example, the user may use programmer 24 to retrieve information from IMD 16 regarding other sensed physiological parameters of patient 14 or information derived from sensed physiological parameters, such as intracardiac or intravascular pressure, activity, posture, tissue oxygen levels, blood oxygen levels, respiration, tissue perfusion, heart sounds, cardiac electrogram (EGM), intracardiac impedance, or thoracic impedance. In some examples, the user may use programmer 24 to retrieve information from IMD 16 regarding the performance or integrity of IMD 16 or other components of system 10A, or a power source of IMD 16. As another example, the user may interact with programmer 24 to program, e.g., select parameters for, therapies provided by IMD 16, such as pacing and, optionally, neurostimulation.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a telemetry head that may be placed proximate to the patient's body near the IMD 16 implant site in order to improve the quality or security of communication between IMD 16 and programmer 24.

Programmer 24, shown and described in more detail below with respect to FIGS. 2-12, includes a computer module and a mating medical device module. The computer module includes a user interface with a touchscreen, and the patient programming module includes telemetry and/or electrodcardiography (ECG) functions of the programmer. The computer module may be configured to store therapy delivery and sensing parameters and history as well as other patient data. The computer module and the medical device module may mate to form a congruent external surface of the programmer.

Distributing the functions of a programmer into a computer module and a medical device module may provide one or more advantages. As one example, the life cycle of a programmer may be significantly greater than the life cycle of computer components used in the manufacture of the programmer. For example, a programmer may include many different computer components such as memory, hard drive, processor, peripheral device interface and other interfaces, battery. By separating the computer module functions from a medical device module that directly interacts with the IMD, the design of the programmer can be more easily changed to include new computer hardware components than if the programmer is a single integrated device. This can reduce the cost of a programmer over the life cycle of a programmer design as well as provide for increased performance of programmers utilizing the same general design but including newly available computer hardware components. If computer components utilized in an initial design of programmer became unavailable, there can be a significant cost to modify the design; however, this cost is mitigated if only the computer module design is modified. For example, medical devices that directly communicate with IMDs may undergo an extensive regulatory approval process. In a programmer having a medical device module separate from a computer module that can only communicate with the IMD via the medical device module, computer hardware upgrades and design changes to computer module may undergo less regulatory scrutiny than computer hardware upgrades and design changes to a unitary programmer.

As another example, the computer module may have substantially similar hardware to that of a commercially available tablet computer. In such an example, the design costs of the tablet computer may be leveraged to reduce the design costs for the programmer. For example, the computer module may include a circuit board having a substantially similar layout to that of a commercially available tablet computer. In such an example, the computer module may include different software than the commercially available tablet computer to limit the functionality of the computer module. For example, the computer module may include a BIOS or other software or firmware, that only allows specific programs or processes to run on the computer module. This may prevent unneeded programs from utilizing system resources of the computer module and reduce the susceptibility of the computer module to system instability from untested software and viruses.

The configuration of system 10 illustrated in FIG. 1 is merely one example. In other examples, a system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12. For each of these examples, any number of the medical leads may include a set of active fixation tines on a distal end of the medical lead in accordance with the techniques described herein.

In addition, in other examples, a system may include any suitable number of leads coupled to IMD 16, and each of the leads may extend to any location within or proximate to heart 12. For example, other examples of systems may include three transvenous leads located as illustrated in FIG. 1, and an additional lead located within or proximate to left atrium 36. Other examples of systems may include a single lead that extends from IMD 16 into right atrium 26 or right ventricle 28, or two leads that extend into a respective one of the right ventricle 28 and right atrium 26. Any electrodes located on these additional leads may be used in sensing and/or stimulation configurations.

As another example, programmer 16 may be used with other IMDs. For example, programmer 16 may be used in a system with leadless sensors or cardiac stimulators or in a system with an infusion device, such as an implantable drug pump that delivers a therapy fluid to a patient.

Figure 2:
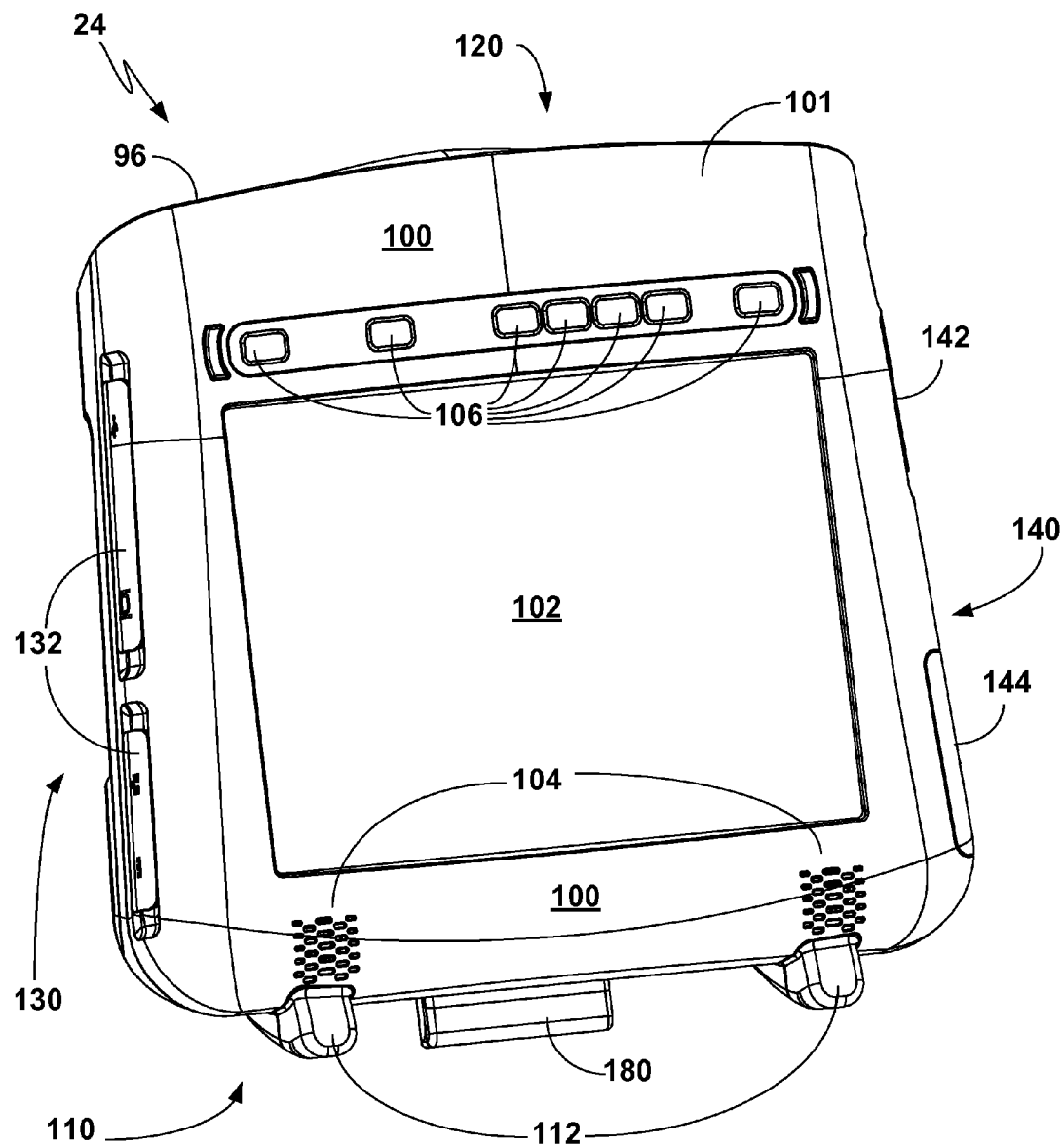
FIG. 2 illustrates an example remote handheld medical device programmer including a computer module and separate medical device module, wherein the computer module housing and the medical device module housing combine to form a congruent external surface of the programmer.

FIGS. 2-11 illustrate components programmer 24. Programmer 24 is a handheld medical device programmer including computer module 96 and a separate medical device module 98. FIG. 2 illustrates front side 100 of programmer 24, including touchscreen 102. As an example, touchscreen 102 may have viewable area diagonal dimension of approximately twelve inches, although touchscreens of other sizes may also be used. FIG. 2 also indicates bottom 110, top 120, left side 130, and right side 140. As referred to herein, the sides of programmer 24 are labeled relative to touchscreen 102.

Only computer module 96 is visible in FIG. 2, with the exception of kickstand 180, which is part of medical device module 98. Computer module 96 includes computer module housing 101, which encases the electronic components of computer module 96. As shown in FIG. 2, front side 100 of programmer 24 includes a user interface with touchscreen 102, speakers 104 and buttons 106. As examples, buttons 106 may be used to initiate one or more following operations: on/off, WiFi on/off, activate barcode reader, emergency notification and initiate an online print session. Feet 112 are on bottom 110 and provide shock protection for programmer 24. FIG. 2 also indicates left side connector covers 132 and right side connector cover 142. These connector covers may fit within connectors on the sides of computer module 96 and serve to protect the connectors, e.g., from dirt and impacts.

Figure 3:
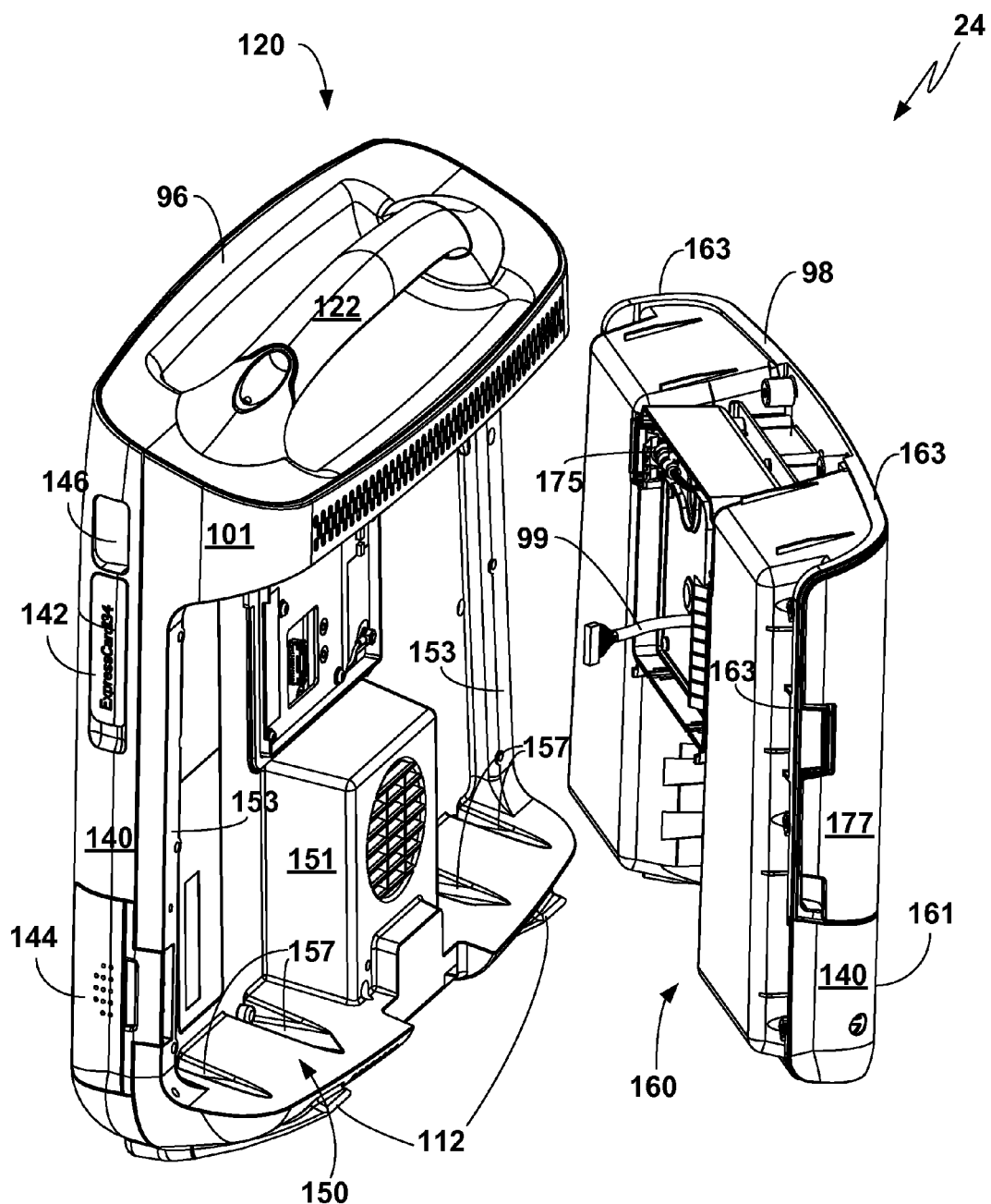
FIG. 3 illustrates an exploded view of the programmer of FIG. 2 with the medical device module separated from the computer module.
Figure 4:
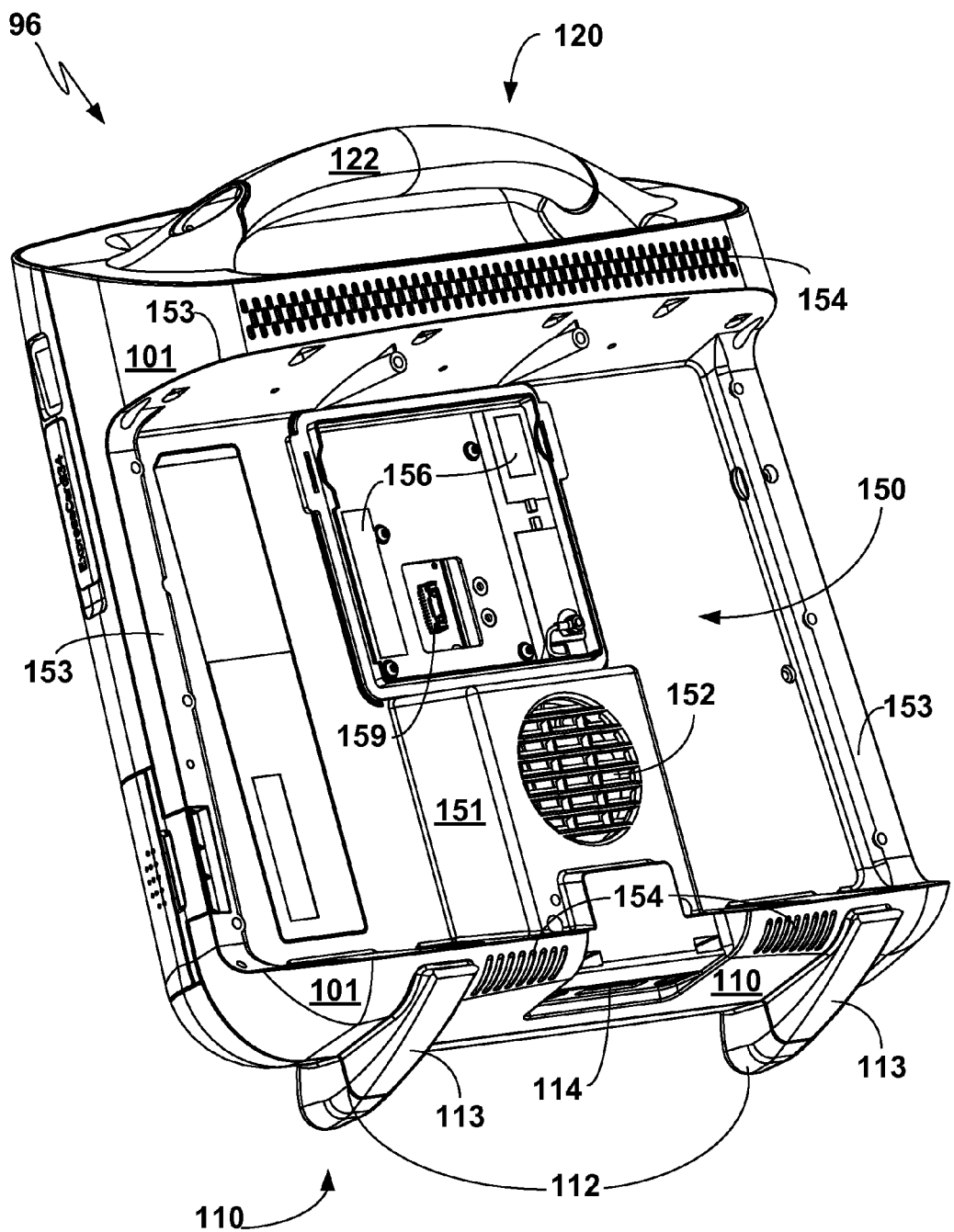
FIG. 4 illustrates the computer module of the programmer of FIG. 2.
Figure 5:
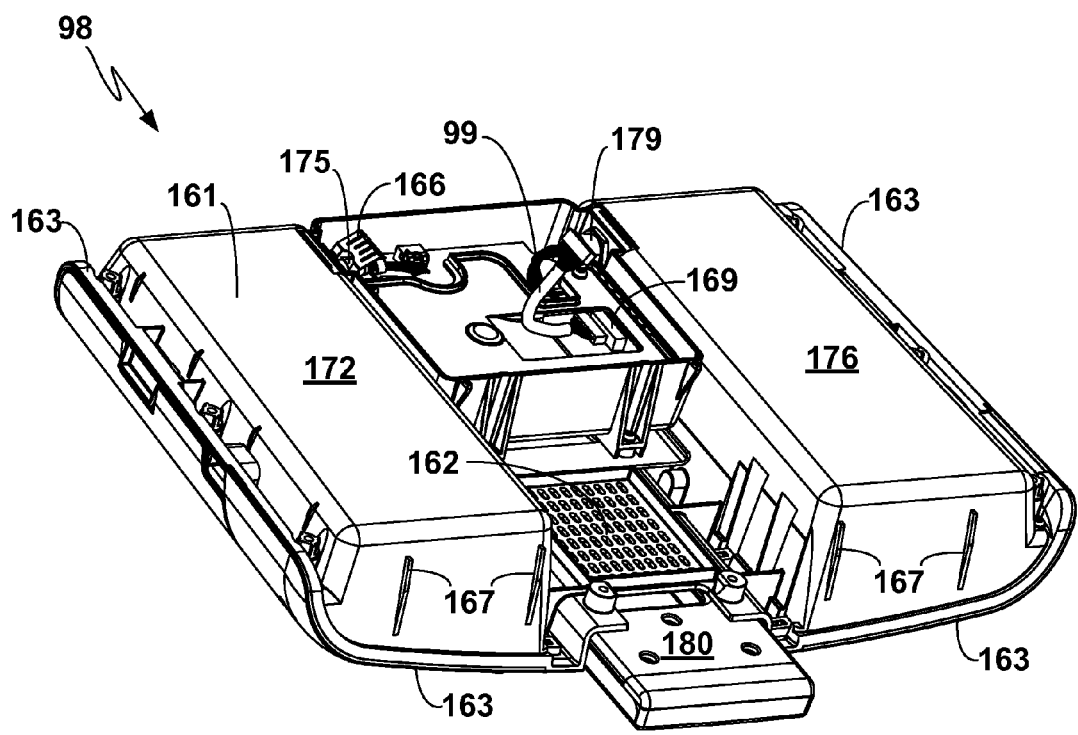
FIG. 5 illustrates the medical device module of the programmer of FIG. 2.

FIG. 3 illustrates an exploded view of the programmer 24 with medical device module 98 separated from the computer module 96, whereas FIG. 4 illustrates computer module 96 and FIG. 5 illustrates medical device module 98. Computer module housing 101 defines recess 150 in computer module 96, which is configured to receive medical device module housing 161. Programmer 24, further includes cable 99, which connects to connector 159 (FIG. 4) on computer module 96 and connector 169 (FIG. 5) on medical device module 98. Cable 99 handles all communications between medical device module 98 and computer module 96. In one example, cable 99, connector 159 and connector 169 may conform to a proprietary connection specification. Using a proprietary connection instead of a standard computer interface may make it difficult to interact with medical device module 98 with device other than computer module 96 (such as standard computer), thereby increasing the security and reliability of medical device module 98.

Top 120, bottom 110 and recess 150 of computer module 96 are each shown in FIG. 4. Handle 122 is located on top 120 of computer module 96. Handle 122 allows for easy transport of programmer 24. In one example, handle 122 may be formed from a molded elastomer and provide shock protection for programmer 24.

Bottom 110 includes docking station connector 114 and feet 112. Feet 112 provide the base of programmer 24 and may also be formed from a molded elastomer to provide shock protection for programmer 24. In one example, feet 112 may be hollow to provide shock protection for programmer 24. As described in greater detail with respect to FIGS. 9-10, Feet 112 form a convex outer surface 113 that provides an about consistent contact surface area to support programmer 24 at any angle between an upright position (FIG. 9) and a reclined position (FIG. 10).

Connector 159 and cooling fan 151 are located within recess 150. Cooling fan 151 operates to cool electronic components of computer module 96. Cooling fan 151 includes fan grate 152, which provides the airflow outlet of for cooling fan 151. As further shown in FIG. 4, the back side of computer module 96 includes airflow inlets 154 above and below recess 150 to allow air into housing 101 of computer module 96.

Ground plane pads 156 are also located within recess 150 and are configured to mate with ground clips of medical device module 98 to provide electrical grounding of medical device module 98. As an example, ground clip 166 is shown in FIG. 5.

Figure 6:
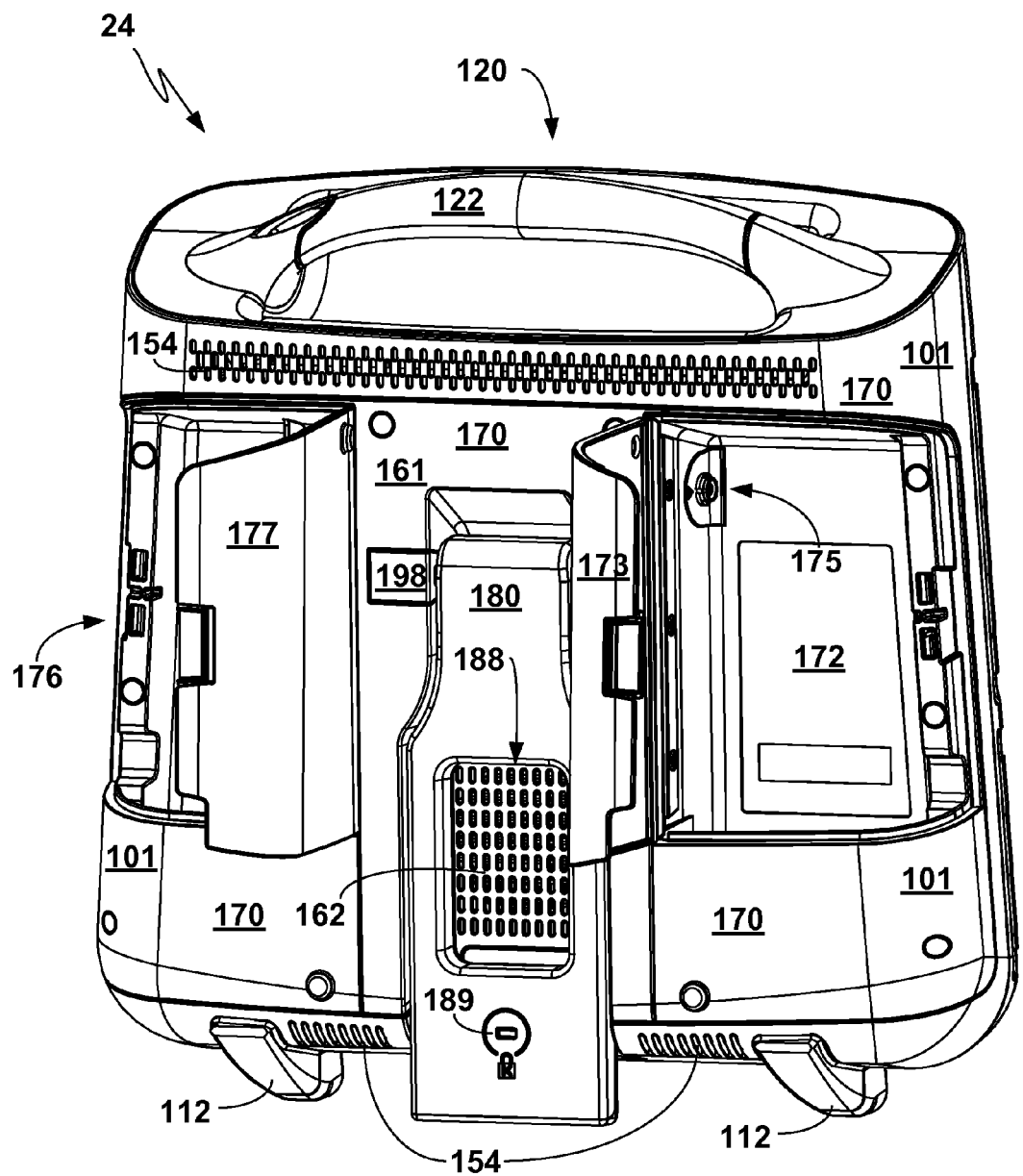
FIG. 6 illustrates a rear view of the programmer of FIG. 2 showing the medical device module with an open electrocardiogram (ECG) cable bay door and an open telemetry head cable bay door.
Figure 7:
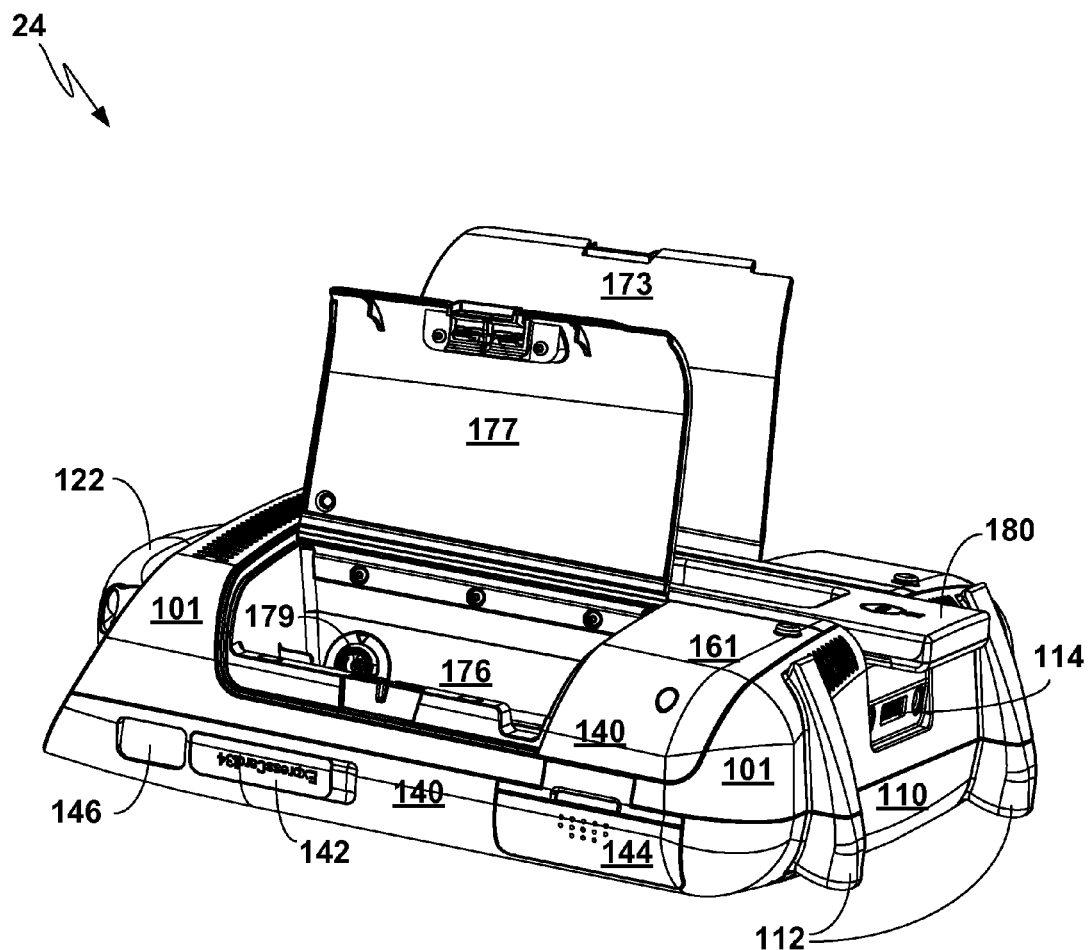
FIG. 7 illustrates a side view of the programmer of FIG. 2 showing a telemetry head cable interface connector within the telemetry head cable bay of the medical device module.
Figure 8:
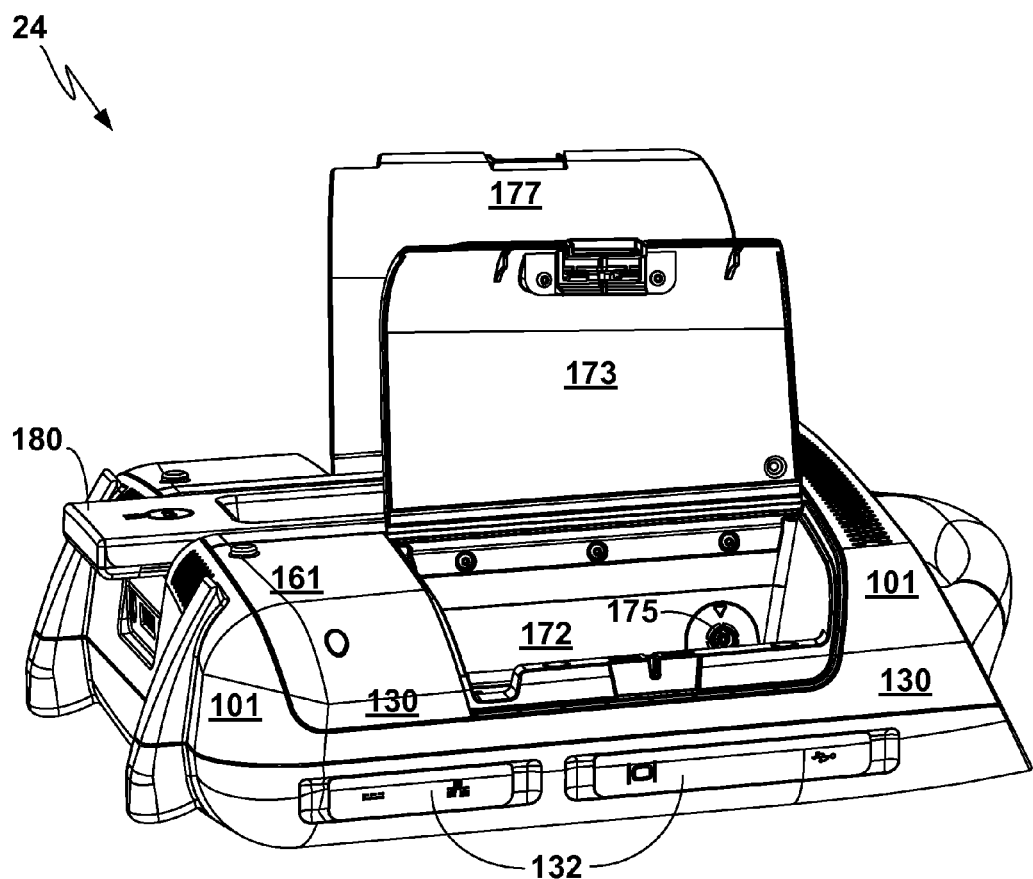
FIG. 8 illustrates a side view of the programmer of FIG. 2 showing an ECG cable interface connector within the ECG bay of the medical device module.

Recess 150 is configured to receive medical device module housing 161 such that computer module housing 101 and medical device module housing 161 combine to form a congruent external surface of programmer 24. For example, as shown in FIG. 6, the back side 170 of programmer 24 includes both computer module housing 101 and medical device module housing 161. As another example, as shown in FIG. 7, the right side 140 of programmer 24 includes both computer module housing 101 and medical device module housing 161 and, as shown in FIG. 8, the left side 130 of programmer 24 includes both computer module housing 101 and medical device module housing 161.

Recess 150 of computer module 96 includes features to align medical device module 98 with computer module 96 to provide a congruent external surface of programmer 24. For example, grooves 157 (FIG. 3) are formed in recess 150 and are configured to mate with protrusions 167 (FIG. 5) of medical device module 98. As another example, sides 153 of recess 150 have the same shape and profile as sides 163 (FIG. 5) of medical device module 98. Sides 153 also include threaded screw holes that align with holes in medical device module 98 to facilitate attaching medical device module 98 to computer module 96 within recess 150.

The interior surface of medical device module 98 is shown in FIG. 5. The interior surface of medical device module 98 is formed by medical device module housing 161 and includes the underside of telemetry head cable bay 172 and the underside of electrocardiogram (ECG) cable bay 176. Telemetry head cable interface connector 175 extends through the sidewall of telemetry head cable bay 172 and ECG cable interface connector 179 extends through the sidewall of ECG cable bay 176.

Medical device module 98 includes fan grate 162, which allows airflow from cooling fan 151 (FIG. 4) to pass through medical device module 98. Fan grate 162 is positioned between ECG cable bay 176 and telemetry head cable bay 172. Kickstand 180 is shown in a fully-collapsed position in FIG. 5. Kickstand 180 includes aperture 188 (FIG. 6), which is adjacent fan grate 162 when kickstand 180 is in the fully-collapsed position. Aperture 188 allows airflow from the cooling fan 151 to pass through fan grate 162 when kickstand 180 is in the fully-collapsed position.

FIG. 5 further illustrates connector 169, which provides a connection from medical device module 98 to computer module 96 via cable 99 and ground clip 166, which provides grounding for medical device module 98 via a ground plane 156 of computer module 96 when medical device module 98 is within recess 150.

FIG. 6 illustrates back side 170 of programmer 24 with ECG cable bay door 177 and telemetry head cable bay door 173 being open. ECG cable bay door 177 provides access to ECG cable bay 176, and telemetry head cable bay door 173 provides access to telemetry head cable bay 172. Telemetry head cable interface connector 175 is within telemetry head cable bay 172 and ECG cable interface connector 179 (FIG. 7) is within ECG cable bay 176.

FIG. 7 illustrates right side 140 of programmer 24 and depicts telemetry head cable interface connector 179 within telemetry head cable bay 172. Similarly, FIG. 8 illustrates left side 130 of programmer 24 and depicts telemetry head cable interface connector 175 within ECG bay 172. Telemetry head cable interface connector 175 is adapted to be coupled with a telemetry head cable and telemetry head cable bay 172 is sized to hold a telemetry head cable (not shown). For example, a telemetry head cable may include a first end adapted to be coupled with telemetry head cable interface connector 175 and a second end including a telemetry head with an antenna configured to send and receive communications with IMD 16 (FIG. 1) through the skin of patient 14 (FIG. 1). Similarly, ECG cable interface connector 179 is adapted to be coupled with an ECG cable and ECG cable bay 176 is sized to hold an ECG cable (not shown). An ECG cable may include a first end adapted to be coupled with ECG cable interface connector 179 and a second end including transcutaneous ECG electrodes configured to be applied to the skin of patient 14 to sense electrical signals of patient 14.

Figure 9:
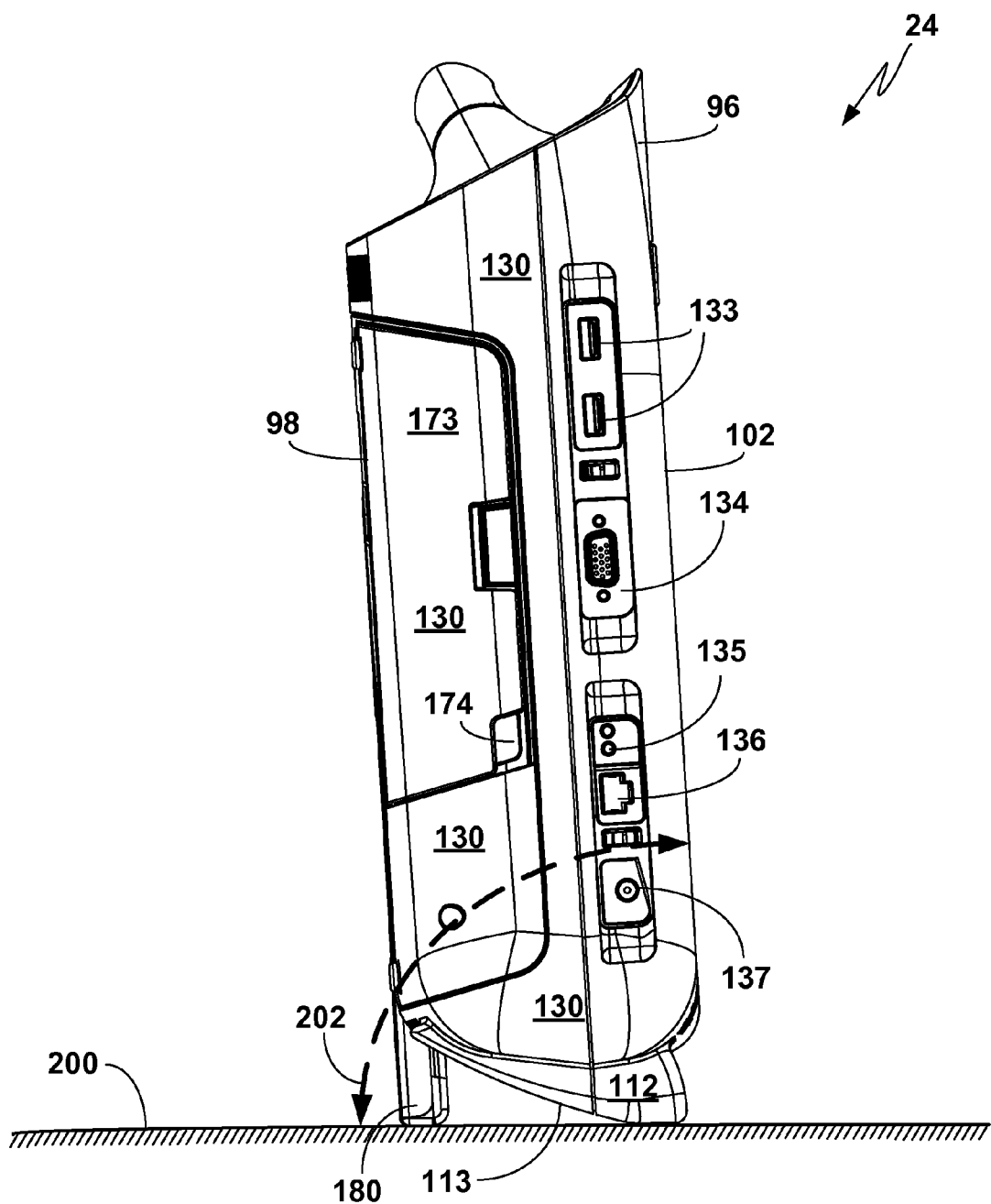
FIG. 9 illustrates a side view of the programmer of FIG. 2 showing the programmer supported in an upright position by two feet of the computer module and a kickstand of the medical device module in a fully-collapsed position.
Figure 10:
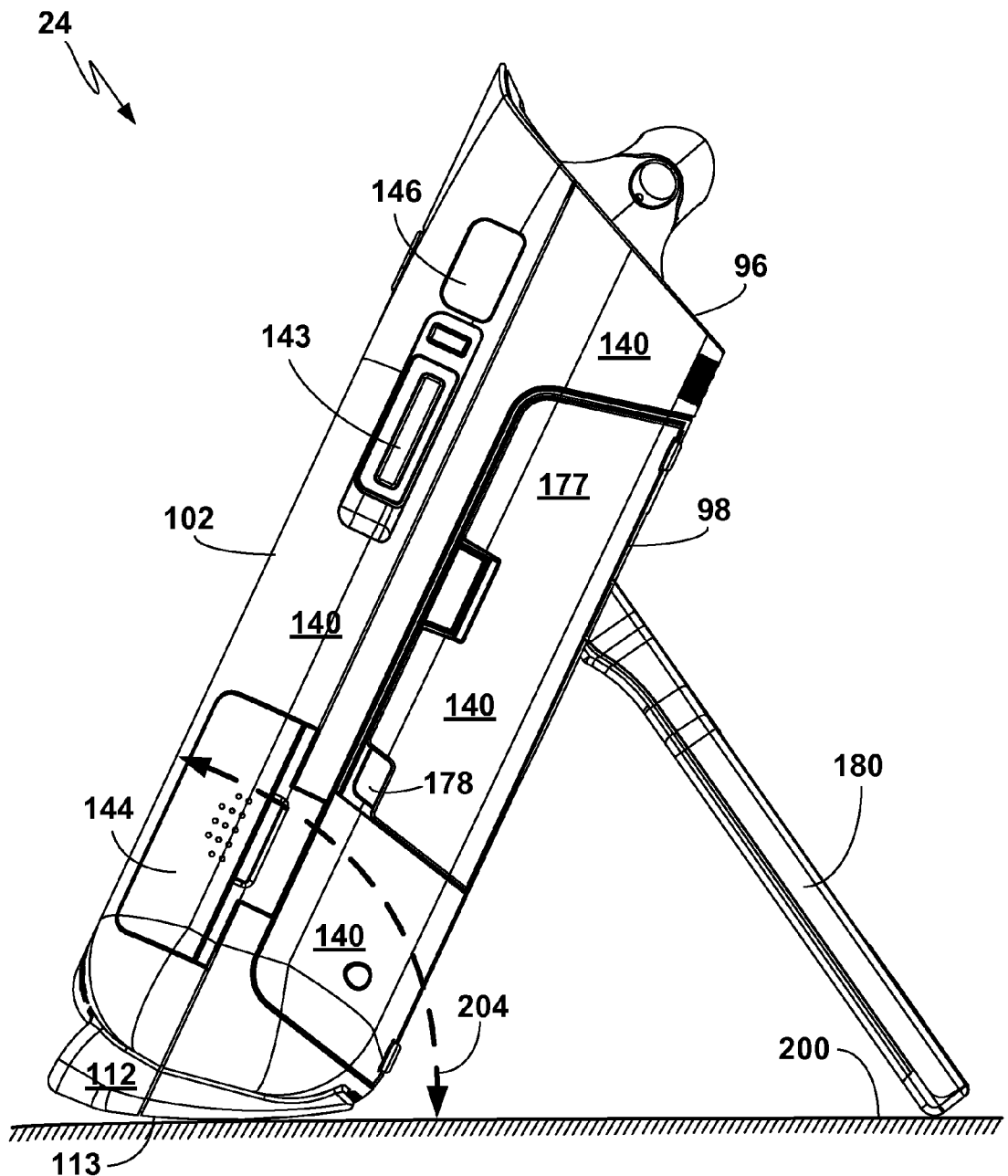
FIG. 10 illustrates a side view of the programmer of FIG. 2 showing the programmer supported in an reclined position by two feet of the computer module and a kickstand of the medical device module in an extended position.

As shown in FIG. 9, left side 130 of programmer 24 includes a plurality of connectors in computer module 96. For example, left side 130 of programmer 24 includes peripheral device interfaces 133, which may be, e.g., a universal serial bus (USB) port such as a port meeting USB 1.1, USB 2.0, USB 3.0, Mini-USB, or Micro-USB specifications. Left side 130 of programmer 24 further includes video interface 143, which may be a Video Graphics Array (VGA) connector, a High-Definition Multimedia Interface (HDMI) connector, a Separate Video (S-Video) connector or another connector. In addition, left side 130 of programmer 24 further includes audio jacks 135, which may include microphone and/or headphone capabilities, computer networking port 136, which may be an RJ-45 port to provide an Ethernet connection, and power supply jack 137, which may be configured to receive either alternating current or direct current to power computer module 96, medical device module 98 and/or charge battery 144. FIG. 9 also illustrates telemetry head cable bay door 173 in a closed position and shows cable aperture 174, which provides access to telemetry head cable bay 172.

As shown in FIG. 10, right side 140 of programmer 24 includes bar code reader 146, computer expansion card slot 143, which may conform to Peripheral Component Interconnect (PCI) PCI express, PCI extended, or other computer expansion card specifications, and a slot to receive battery 144. FIG. 10 also illustrates ECG cable bay door 177 in a closed position and shows cable aperture 178, which provides access to ECG cable bay 176.

FIG. 9 illustrates left side 130 of programmer 24 with programmer 24 supported on substantially flat surface 200 in an upright position by feet 112 of computer module 96 and kickstand 180 of medical device module 98. Kickstand 180 is in a fully-collapsed position in FIG. 9. In contrast, FIG. 10 illustrates left side 140 of programmer 24 with programmer 24 supported on substantially flat surface 200 in a reclined position by feet 112 of computer module 96 and kickstand 180 of medical device module 98. Kickstand 180 is in an extended position in FIG. 10.

When kickstand 180 is in a fully-collapsed position, and programmer 24 is supported on substantially flat surface 200 in a reclined position, angle 202 (FIG. 9) may be between eighty and ninety degrees. For example, angle 204 may be about eighty-seven degrees.

Feet 112 form a convex outer surface 113 that provides an about consistent contact surface area to support programmer 24 at any angle between the upright position and the reclined position. The configuration of feet 112 and convex outer surface 113 in particular provides sufficient grip force for programmer 24 at any angle between the upright position and the reclined position.

Figure 11:
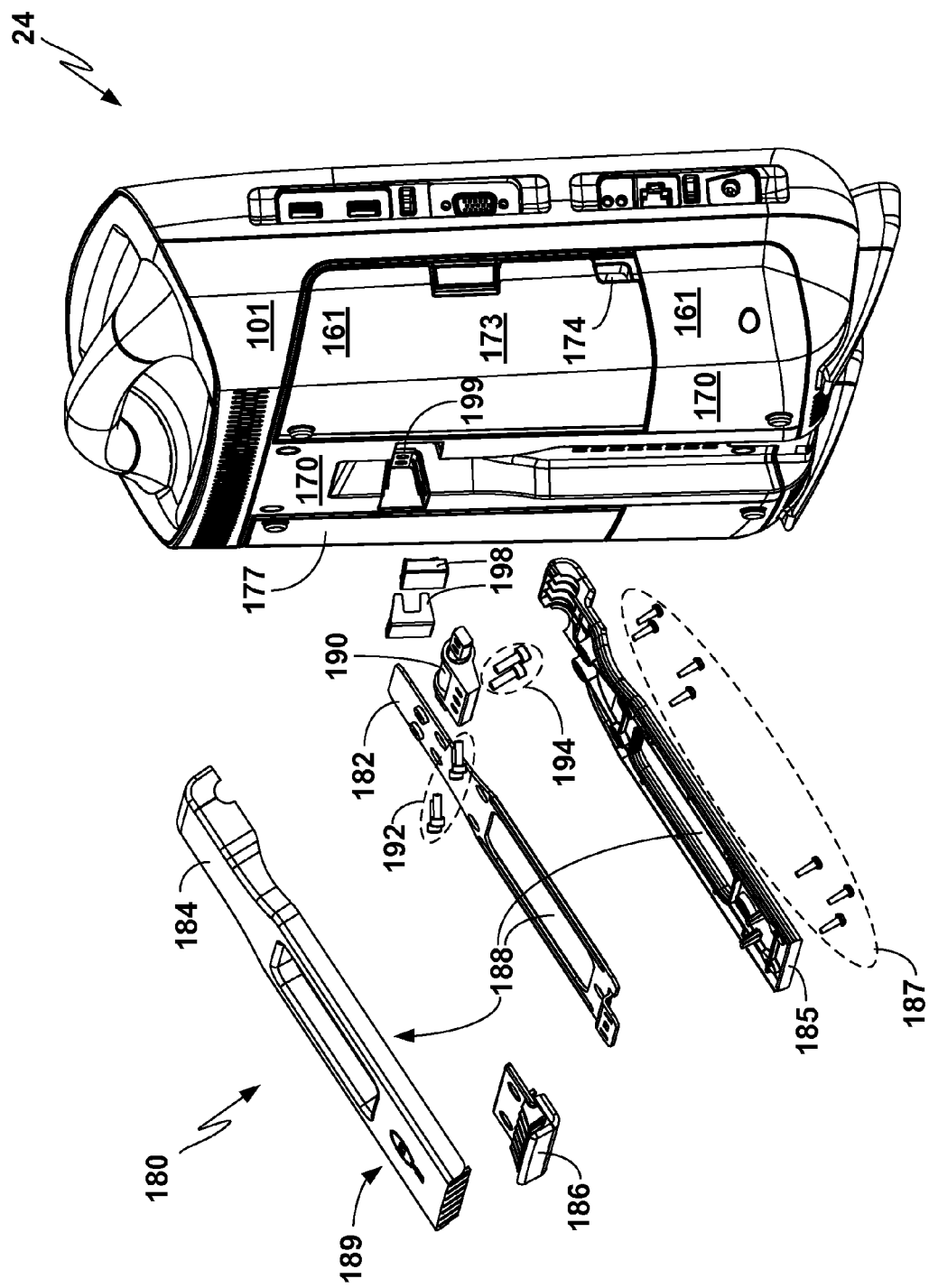
FIG. 11 illustrates the programmer of FIG. 2 with an exploded view of the kickstand components.

FIG. 11 illustrates programmer 24 with an exploded view of components of kickstand 180. As shown in FIG. 11, kickstand 180 is connected to medical device module housing 161 with friction hinge 190. Hinge mounting screws 192 secure friction hinge 190 to metal mounting plate 199 in medical device module housing 161. Covers 198 snap in place within medical device module housing 161 to cover screws 192 and metal mounting plate 199. When mounted to metal mounting plate 199 by screws 192, friction hinge 190 is in direct contact with metal mounting plate 199. This configuration mitigates "creep" which can occur when plastic components are under strain over time as compared to a design in which friction hinge 190 compresses a plastic component of medical device module housing 161 when mounted to medical device module housing 161.

Kickstand 180 is formed from metal insert 182, which is covered by upper molded plastic cover 184, and lower molded plastic cover 185. Metal insert 182 extends substantially the entire length of kickstand 180. Kickstand 180 further includes molded elastomer foot 186, which may have a lower durometer than upper molded plastic cover 184, and lower molded plastic cover 185 to increase friction between kickstand 180 and a supporting surface. Metal insert 182, upper molded plastic cover 184, lower molded plastic cover 185 and molded elastomer foot 186 are held together with screws 187, and kickstand is attached to friction hinge 190 by screws 194.

Metal insert 182, upper molded plastic cover 184 and lower molded plastic cover 185 combine to form aperture 188, which allows airflow from cooling fan 151 (FIG. 3) to pass through fan grate 162 (FIG. 6) when kickstand 180 is in the fully-collapsed position. Metal insert 182 and upper molded plastic cover 184 also combine to form Kensington security slot 189, which may be used to lock programmer 24 using a standard Kensington lock.

Friction hinge 190 provides infinite adjustability for kickstand 180 between the upright and reclined positions. Further, friction hinge 190 provides sufficient opening resistance at every position between the upright position and the reclined position to allow a user to provide user inputs to programmer 24 by pressing on touch screen 102 without causing kickstand 180 to extend further when programmer 24 is supported by feet 112 and kickstand 180 on a flat surface. Molded elastomer foot 186 and feet 112 may have a durometer of about seventy Shore A to provide adequate friction to support programmer 24.

In some example, friction hinge 190 may provide a greater opening resistance than closing resistance. For example, friction hinge 190 may provide an opening resistance least 50 percent greater than the closing resistance of friction hinge 190. As another example, friction hinge 190 may provide an opening resistance of about twenty in-lbs and a closing resistance of about fourteen in-lbs.

Figure 12:
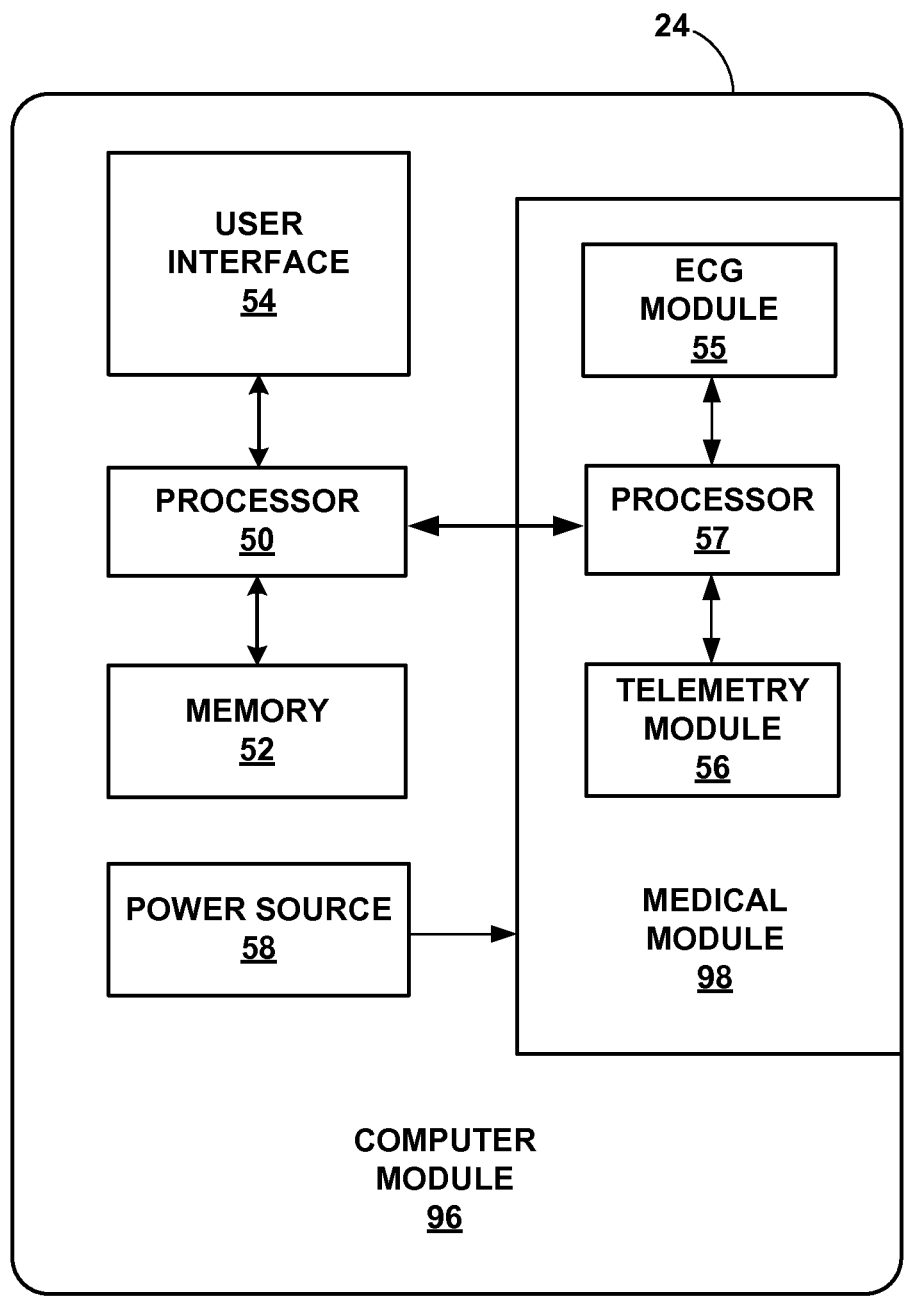
FIG. 12 is a block diagram of an example external programmer including a computer module and separate medical device module.

FIG. 12 is a block diagram of an example configuration of programmer 24. FIG. 12 illustrates functional components of computer module 96 and medical device module 98. Computer module 96 includes user interface 54, which may include a touchscreen that displays data received from IMD 16 (FIG. 1) and receive input from a user. Computer module 96 also includes memory 52, which may store selectable patient therapy and sensing parameters for IMD 16 as well as therapy and sensing history information other patient data. Processor 50 receives user input from user interface 54 and communicates with medical device module 98 via a computer module interface, such as connector 159 (FIG. 4) and a medical device module interface, such as connector 169 (FIG. 5) of medical device module 98. As discussed previously, connector 159 of computer module 96 is in electrical communication with connector 169 of medical device module 98 via cable 99.

Computer module 96 further includes power source 58, which may be a rechargeable power source. Both medical device module 98 and computer module 96 are powered by power source 58. In this manner, medical device module 98 is dependent on being connected to computer module 96 to operate.

Medical device module 98 includes ECG module 55 and telemetry module 56, which are controlled by medical device module processor 57. ECG module 55 includes an ECG cable interface connector adapted to be coupled with an ECG cable, such as ECG cable interface connector 179 (FIG. 7), and ECG signal interface circuitry that converts analog ECG signals from the ECG cable interface connector to digital ECG signals that correspond to the analog ECG signals.

Telemetry module 56 wirelessly communicates with 16. Medical device module processor 57 operates to forward communications between computer module processor 50 and IMD 16 via telemetry module 56 and connector 169. Programming commands or data are transmitted between an IPG telemetry antenna within IPG 12 and a telemetry head telemetry antenna within telemetry head 20 during a telemetry uplink transmission 28 or downlink transmission 30. In a telemetry uplink transmission 28, the telemetry head telemetry antenna operates as a telemetry receiver antenna, and the IPG telemetry antenna operates as a telemetry transmitter antenna. Conversely, in a telemetry downlink transmission 30, the telemetry head telemetry antenna operates as a telemetry transmitter antenna, and the IPG telemetry antenna operates as a telemetry receiver antenna.

Programmer 24 is typically employed during implantation of an IMD to program initial operating modes and parameter values and to obtain implant patient data for the patient's medical record. Programmer 24 is also employed from time to time during routine patient follow-up visits or when a clinical issue arises causing the patient to seek medical assistance in order to uplink telemeter patient data and IMD operating stored data to the programmer for analysis. In use, the attending medical care giver applies the ECG skin electrodes to the patient's body and/or holds telemetry head against the patient's skin and over the IMD 16 to align the transceiver antennas in each as close together and as still as possible to ensure reliable telemetry transmission.

A user may use programmer 24 to select therapy programs (e.g., sets of stimulation parameters), generate new therapy programs, or modify therapy programs for IMD 16. The clinician may interact with programmer 24 via user interface 54.

Processor 50 can take the form of one or more microprocessors, DSPs, ASICs, FPGAs, programmable logic circuitry, or the like, and the functions attributed to processor 50 in this disclosure may be embodied as hardware, firmware, software or any combination thereof. Memory 52 may store instructions and information that cause processor 50 to provide the functionality ascribed to programmer 24 in this disclosure. Memory 52 may include any fixed or removable magnetic, optical, or electrical media, such as RAM, ROM, CD-ROM, hard or floppy magnetic disks, EEPROM, or the like. Memory 52 may also include a removable memory portion that may be used to provide memory updates or increases in memory capacities. A removable memory may also allow patient data to be easily transferred to another computing device, or to be removed before programmer 24 is used to program therapy for another patient. Memory 52 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 56, which may be coupled to an internal antenna or an external antenna. An external antenna that is coupled to programmer 24 may correspond to the telemetry head that may be placed over heart 12.

Telemetry module 56 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth® specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, processor 50 of programmer 24 configured to perform any of the following techniques: analyze data from IMD 16, calibrate sensing and/or therapy delivery functions of IMD 16, present data to the user via the user interface 54 for review or analysis, provide instructions to the user via user interface 54, provide alarms to the user via user interface 54, store selectable therapy delivery and/or sensing parameters of the IMD memory 52, provide an indication of therapy delivery parameters selected by the user to IMD 16 via medical device module 98 and/or store a therapy delivery and/or sensing history of IMD 16 in memory 52.

Figure 13:
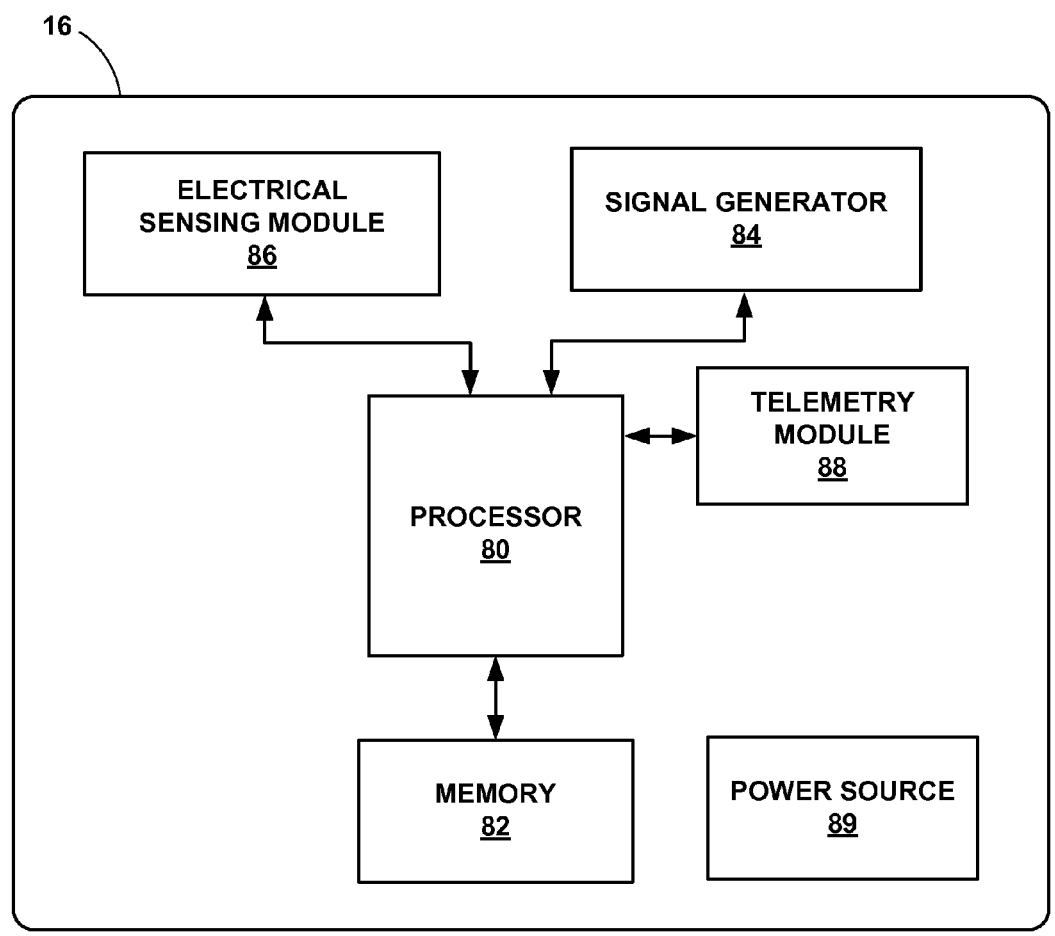
FIG. 13 is a functional block diagram illustrating an example configuration of an IMD.

FIG. 13 is a functional block diagram illustrating one example configuration of IMD 16 of FIG. 1. In the example illustrated by FIG. 13, IMD 16 includes a processor 80, memory 82, signal generator 84, electrical sensing module 86, telemetry module 88, and power source 89. Memory 82 may include computer-readable instructions that, when executed by processor 80, cause IMD 16 and processor 80 to perform various functions attributed to IMD 16 and processor 80 herein. Memory 82 may be a computer-readable storage medium, including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 in this disclosure may be embodied as software, firmware, hardware or any combination thereof. Processor 80 controls signal generator 84 to deliver stimulation therapy to heart 12 according to operational parameters or programs, which may be stored in memory 82. For example, processor 80 may control signal generator 84 to deliver electrical pulses with the amplitudes, pulse widths, frequency, or electrode polarities specified by the selected one or more therapy programs.

Signal generator 84, as well as electrical sensing module 86, is electrically coupled to electrodes of IMD 16 and/or leads coupled to IMD 16. In the example illustrated in FIG. 13, signal generator 84 is configured to generate and deliver electrical stimulation therapy to heart 12. For example, signal generator 84 may deliver pacing, cardioversion, defibrillation, and/or neurostimulation therapy via at least a subset of the available electrodes. In some examples, signal generator 84 delivers one or more of these types of stimulation in the form of electrical pulses. In other examples, signal generator 84 may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver stimulation signals, e.g., pacing, cardioversion, defibrillation, and/or neurostimulation signals. The switch module may include a switch array, switch matrix, multiplexer, or any other type of switching device suitable to selectively couple a signal to selected electrodes.

Electrical sensing module 86 monitors signals from at least a subset of the available electrodes, e.g., to monitor electrical activity of heart 12. Electrical sensing module 86 may also include a switch module to select which of the available electrodes are used to sense the heart activity. In some examples, processor 80 may select the electrodes that function as sense electrodes, i.e., select the sensing configuration, via the switch module within electrical sensing module 86, e.g., by providing signals via a data/address bus.

In some examples, electrical sensing module 86 includes multiple detection channels, each of which may comprise an amplifier. Each sensing channel may detect electrical activity in respective chambers of heart 12, and may be configured to detect either R-waves or P-waves. In some examples, electrical sensing module 86 or processor 80 may include an analog-to-digital converter for digitizing the signal received from a sensing channel for electrogram (EGM) signal processing by processor 80. In response to the signals from processor 80, the switch module within electrical sensing module 86 may couple the outputs from the selected electrodes to one of the detection channels or the analog-to-digital converter.

During pacing, escape interval counters maintained by processor 80 may be reset upon sensing of R-waves and P-waves with respective detection channels of electrical sensing module 86. Signal generator 84 may include pacer output circuits that are coupled, e.g., selectively by a switching module, to any combination of the available electrodes appropriate for delivery of a bipolar or unipolar pacing pulse to one or more of the chambers of heart 12. Processor 80 may control signal generator 84 to deliver a pacing pulse to a chamber upon expiration of an escape interval. Processor 80 may reset the escape interval counters upon the generation of pacing pulses by signal generator 84, or detection of an intrinsic depolarization in a chamber, and thereby control the basic timing of cardiac pacing functions. The escape interval counters may include P-P, V-V, RV-LV, A-V, A-RV, or A-LV interval counters, as examples. The value of the count present in the escape interval counters when reset by sensed R-waves and P-waves may be used by processor 80 to measure the durations of R-R intervals, P-P intervals, P-R intervals and R-P intervals. Processor 80 may use the count in the interval counters to detect heart rate, such as an atrial rate or ventricular rate. In some examples, an IMD may include one or more sensors in addition to electrical sensing module 86. For example, an IMD may include a pressure sensor and/or an oxygen sensor (for tissue oxygen or blood oxygen sensing).

Telemetry module 88 includes any suitable hardware, firmware, software or any combination thereof for communicating with another device, such as programmer 24 (FIGS. 1 and 2). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and receive downlinked data from programmer 24 via an address/data bus. In some examples, telemetry module 88 may provide received data to processor 80 via a multiplexer.

The techniques described in this disclosure may be applicable to IMDs that support sensing and delivery of therapy. In other examples, the techniques may be applicable to IMDs that provide sensing only. The techniques described in this disclosure, including those attributed to IMD 16 and programmer 24, or other elements such as modules or components of such devices, may be implemented, at least in part, in hardware, software, firmware or any combination thereof. Even where functionality may be implemented in part by software or firmware, such elements will be implemented in a hardware device. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a non-transitory computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A medical device programmer comprising:
   a medical device module comprising:
   a medical device module housing including mating features;
   a telemetry module that wirelessly communicates with an implantable medical device (IMD) that delivers therapy to a patient;
   a medical device module interface; and
   a medical device module processor that communicates with the IMD via the telemetry module; and
   a computer module comprising:
   a computer module housing including complimentary mating features that compliment the mating features of the medical device module housing such that the computer module housing and the medical device module housing combine to form a congruent external surface of the programmer, wherein the computer module housing includes a base, at least two feet on the base, the at least two feet forming a convex outer surface and configured to provide an about consistent contact surface area to support the programmer at any angle between the upright position and the reclined position;
   a user interface including a touchscreen that displays data received from the IMD and receives input from a user;
   a memory that stores selectable patient therapy parameters for the IMD;
   a computer module interface in electrical communication with the medical device module interface; and
   a computer module processor that communicates with the medical device module via the computer module interface,
   wherein the medical device module processor forwards communications between the computer module processor and the IMD via the medical device module interface and the telemetry module.

2. The programmer of claim 1, wherein the medical device module further comprises an electrocardiogram (ECG) module, wherein the ECG module includes:
- an ECG cable interface connector adapted to be coupled with an ECG cable; and
- ECG signal interface circuitry that converts analog ECG signals from the ECG cable interface connector to digital ECG signals that correspond to the analog ECG signals.

3. The programmer of claim 2, wherein the medical device module comprises a bay and the medical device module housing includes a bay door that provides access to the bay, wherein the ECG cable interface connector is within the bay.

4. The programmer of claim 3, further comprising an ECG cable having a first end coupled with the ECG cable interface connector and a second end including a plurality of ECG electrodes configured to be applied to the skin of the patient, wherein the ECG cable fits within the bay.

5. The programmer of claim 3,
- wherein the bay is an ECG cable bay and the bay door is an ECG cable bay door,
- wherein the medical device module comprises a telemetry head cable bay and the medical device module housing includes a telemetry head cable bay door that provides access to the telemetry head cable bay, and
- wherein the medical device module further comprises a telemetry head cable interface connector adapted to be coupled with a telemetry head cable, wherein the telemetry head cable interface connector is within the telemetry head cable bay.

6. The programmer of claim 5, further comprising a telemetry head cable having a first end coupled with the telemetry head cable interface connector and a second end including a telemetry head with an antenna configured to send and receive communications with the IMD through the skin of the patient,
- wherein the telemetry head cable fits within the telemetry head cable bay.

7. The programmer of claim 6,
- wherein the computer module includes a cooling fan to cool electronic components of the computer module,
- wherein the medical device module includes a fan grate that allows airflow from the cooling fan to pass through the medical device module, and
- wherein the fan grate is positioned between the ECG cable bay and the telemetry head cable bay.

8. The programmer of claim 1,
- wherein the computer module includes a cooling fan to cool electronic components of the computer module, and
- wherein the medical device module includes a fan grate that allows airflow from the cooling fan to pass through the medical device module.

9. The programmer of claim 1, wherein the computer module housing defines a recess configured to receive the medical device module housing such that the computer module housing and the medical device module housing combine to form the congruent external surface of the programmer.

10. The programmer of claim 9, further comprising a set of screws securing the medical device module within the recess of the computer module.

11. The programmer of claim 1, wherein the computer module includes a rechargeable power source, wherein the medical device module is powered by the rechargeable power source of the computer module.

12. The programmer of claim 1, wherein the computer module includes one or more interfaces selected from a group consisting of:
- a computer expansion card slot;
- a docking station connector;
- a barcode reader;
- a video interface;
- a computer networking port;
- a peripheral device interface;
- an audio jack; and
- a power supply jack.

13. The programmer of claim 1, wherein the computer module processor is configured to perform at least one of a group consisting of:
- analyze data from the IMD;
- calibrate the IMD;
- present data to the user via the user interface for review or analysis;
- provide instructions to the user via the user interface;
- provide alarms to the user via the user interface;
- store selectable therapy delivery and/or sensing parameters of the IMD in the memory;
- provide an indication of therapy delivery parameters selected by the user to the IMD via the medical device module; and
- store a therapy delivery and/or sensing history of the IMD in the memory.

14. The programmer of claim 1, wherein the computer module processor receives a user selection of therapy parameters for the IMD from the user via the user interface.

15. The programmer of claim 1, wherein the memory also stores data from the IMD.

16. The programmer of claim 1, wherein the IMD comprises at least one of an infusion device, a cardiac stimulator or a neurostimulator.

17. A system comprising:
- an implantable medical device (IMD) that delivers therapy to a patient; and
- a medical device programmer comprising:
  - a medical device module comprising:
    - a medical device module housing including mating features;
    - a telemetry module that wirelessly communicates with the IMD;
    - a medical device module interface; and
    - a medical device module processor that communicates with the IMD via the telemetry module; and
  - a computer module comprising:
    - a computer module housing including complimentary mating features that complement the mating features of the medical device module housing such that the computer module housing and the medical device module housing combine to form a congruent external surface of the programmer, wherein the computer module housing includes a base, at least two feet on the base, the at least two feet forming a convex outer surface and configured to provide an about consistent contact surface area to support the programmer at any angle between the upright position and the reclined position;
    - a user interface including a touchscreen that displays data received from the IMD and receives input from a user;
    - a memory that stores selectable patient therapy parameters for the IMD;

a computer module interface in electrical communication with the medical device module interface; and a computer module processor that communicates with the medical device module via the computer module interface, wherein the medical device module processor forwards communications between the computer module processor and the IMD via the medical device module interface and the telemetry module.

18. A medical device programmer comprising:

a medical device module comprising:

a medical device module housing including mating features;

a telemetry module that wirelessly communicates with an implantable medical device (IMD) that delivers therapy to a patient;

a telemetry head cable bay with a telemetry head cable bay door in the medical device module housing, the telemetry head cable door providing access to the telemetry head cable bay;

a telemetry head cable interface connector adapted to be coupled with a telemetry head cable, wherein the telemetry head cable interface connector is within the telemetry head cable bay;

an electrocardiogram (ECG) module including an ECG cable interface connector adapted to be coupled with an ECG cable and including ECG signal interface circuitry that converts analog ECG signals from the ECG cable interface connector to digital ECG signals that correspond to the analog ECG signals;

an ECG cable bay with an ECG cable bay door in the medical device module housing, the ECG cable bay door providing access to the ECG cable bay, wherein the ECG cable interface connector is within the ECG cable bay;

a medical device module interface; and a medical device module processor communicates with the IMD via the telemetry module; and a computer module comprising:

a computer module housing including complimentary mating features that compliment the mating features of the medical device module housing such that the computer module housing and the medical device module housing combine to form a congruent external surface of the programmer, wherein the computer module housing includes a base;

at least two feet on the base, the at least two feet forming a convex outer surface and configured to provide an about consistent contact surface area to support the programmer at any angle between the upright position and the reclined position, a user interface including a touchscreen that displays data received from the IMD and receives input from a user;

a memory that stores selectable patient therapy parameters for the IMD;

a computer module interface in electrical communication with the medical device module interface;

a computer module processor that communicates with the medical device module via the computer module interface; and a rechargeable power source, wherein the medical device module is powered by the rechargeable power source of the computer module, wherein the medical device module processor forwards communications between the computer module processor and the IMD via the medical device module interface and the telemetry module.

19. The programmer of claim 18, further comprising:

wherein the medical device module includes an adjustable kickstand on a side of the medical device module housing that opposes the touchscreen, wherein the kickstand is configured to combine with the base to support the programmer in a upright position when the kickstand is fully-collapsed, wherein the kickstand is configured to combine with the base to support the programmer in a reclined position when the kickstand is fully-extended, wherein when the programmer is supported by the kickstand and the base on a flat surface in the upright position with the kickstand fully-collapsed, the touchscreen is at an angle of about 80 degrees to about 90 degrees the flat surface, wherein when the programmer is supported by the kickstand and the base on the flat surface in the reclined position with the kickstand fully-extended, the touchscreen is at an angle of less than about 45 degrees to the flat surface, and wherein the kickstand provides infinite adjustability between the upright and reclined positions.

20. The programmer of claim 18, wherein the at least two feet are hollow and formed from a molded elastomer.

21. The programmer of claim 18, wherein the computer module includes a cooling fan to cool electronic components of the computer module, wherein the medical device module includes a fan grate that allows airflow from the cooling fan to pass through the medical device module, and wherein the fan grate is positioned between the ECG cable bay and the telemetry head cable bay.

* * * * *